United States Patent [19]

Perez-Polo

[11] Patent Number: 5,475,088
[45] Date of Patent: Dec. 12, 1995

[54] NEUROTROPHIC PEPTIDES

[75] Inventor: J. Regino Perez-Polo, Galveston, Tex.

[73] Assignee: Board of Regents, The University of Texas System, Austin, Tex.

[21] Appl. No.: 208,921

[22] Filed: Mar. 10, 1994

Related U.S. Application Data

[62] Division of Ser. No. 852,631, Mar. 17, 1992, abandoned.

[51] Int. Cl.$^6$ ....................................................... C07K 7/08
[52] U.S. Cl. ............................................. 530/326; 530/327
[58] Field of Search ................................. 514/17, 14, 15; 530/326, 327, 328, 329

[56] References Cited

FOREIGN PATENT DOCUMENTS 0335637  4/1989  European Pat. Off. .

OTHER PUBLICATIONS

Lahtinen, *Cell Differentiation and Development*, vol. 26 (1989) 201–9.
Di Stefano et al, *The Journal of Neuroscience* 1988, 231–41.
Rossino et al. Dialog File 55: (C. Biosis 1991).
Radeke et al, *Nature*, v. 325, 12 Feb. 1987.
Welcher et al, PNAS 88 159–163 (1991).
Chandler et al J. Biol. Chem. 259 6882–6889 (1984).
Perez-Polo et al., "Nerve Growth Factor and Neuronal Cell Death," *Molecular Neurobiology*, The Humana Press Inc., pp. 57–91, 1990, published in USA.
Radeke et al., "Gene Transfer and Molecular Cloning of the Rat Nerve Growth Factor Receptor," *Nature*, 325:593–597, 1987, published in the United Kingdom.
Chao et al., "Gene Transfer and Molecular Cloning of the Human NGF Receptor," *Science*, 232:518–521, 1986, published in U.S.A.
Bernd et al., "Localization of High–Affinity and Low–Affinity Nerve Growth Factor Receptors in Cultured Rat Basal Forebrain," *Neuroscience*, 26(1):121–129, 1988, published in Great Britain.
Mufson et al., "Nerve Growth Factor Receptor Immunoreactive Profiles in the Normal, Aged Human Basal Forebrain: Colocalization with Cholinergic Neurons," *The Journal of Comparative Neurology*, 285:196–217, 1989, published in U.S.A.
Hempstead et al., "High–Affinity NGF Binding Requires Coexpression of the *trk* Proto–Oncogene and the Low–Affinity NGF Receptor," *Nature*, 350:678–683, 1991, published in the United Kingdom.
Fischer et al., "Amelioration of Cholinergic Neuron Atrophy and Spatial Memory Impairment in Aged Rats by Nerve Growth Factor," *Nature*, 329:65–68, 1987, published in the United Kingdom.
Ullrich et al., "Human β–nerve Growth Factor Gene Sequence Highly Homologous to that of Mouse," *Nature*, 303:821–825, 1983, published in the United Kingdom.
DiStefano & Johnson, "Nerve Growth Factor Receptors on Cultured Rat Schwann Cells," *The Journal of Neuroscience*, 8(1):231–241, 1988, published in U.S.A.

Grob et al., "Characterization of the Human Melanoma Nerve Growth Factor Receptor," *The Journal of Biological Chemistry*, 260(13):8044–8049, 1985, published in U.S.A.
Green & Greene, "A Single $M_r$~103,000 $^{125}$I–β–Nerve Growth Factor–Affinity–Labeled Species Represent Both the Low and High Affinity Forms of the Nerve Growth Factor Receptor," *The Journal of Biological Chemistry*, 261(32):15316–15326, 1986, published in U.S.A.
Riopelle et al., "Distribution and Characteristics of Nerve Growth Factor Binding on Cholinergic Neurons of Rat and Monkey Forebrain," *Neurochemical Research*, 12(10):923–928, 1987, published in U.S.A.
Gage et al., "Experimental Approaches to Age–Related Cognitive Impairments," *Neurobiology of Aging*, 9:645–655, 1988, published in U.S.A.
Phelps et al., "Commentary: Potential Use of Nerve growth Factor to Treat Alzheimer's Disease," *Neurobiology of Aging*, 10:205–207, 1989, published in U.S.A.
Hefti & Mash, "Localization of Nerve Growth Factor Receptors in the Normal Human Brain and in Alzheimer's Disease," *Neurobiology of Aging*, 10:75–87, 1989, published in U.S.A.
Bruce & Heinrich, "Rapid Communication: Production and Characterization of Biologically Active Recombinant Human Nerve Growth Factor," *Neurobiology of Aging*, 10:89–94, 1989, published in U.S.A.
Marchetti et al., "Binding Constants of Soluble NGF–Receptors in Rat Oligodendrocytes and Astrocytes in Culture," *Biochemical and Biophysical Research Communications*, 147(1):422–427, 1987, published in U.S.A.
Distel et al., "Nucleoprotein Complexes that Regulate Gene Expression in Adipocyte Differentiation: Direct Participation of c–fos," *Cell*, 49:835–844, 1987, published in U.S.A.
Lahtinen, "Age–Dependence of the Nerve Fibre Growth–Promoting Effects of Hippocampus and Exogenous Nerve Growth Factor on Cultured Rat Septum and Superior Cervical Ganglion," *Cell Differentiation and Development*, 26:201–209, 1989, published in Ireland.
Cohen-Cory et al., "Brief Communication: Expression of High– and Low–Affinity Nerve Growth Factor Receptors by Purkinje Cells in the Developing Rat Cerebellum," *Experimental Neurology*, 105:104–109, 1989, published in U.S.A.
Johnson et al., "Expression and Structure of the Human NGF Receptor," *Cell*, 47:545–554, 1986, published in U.S.A.

(List continued on next page.)

*Primary Examiner*—Stephen G. Walsh
*Assistant Examiner*—Arie M. Michelsohn
*Attorney, Agent, or Firm*—Arnold, White & Durkee

[57] ABSTRACT

The present invention involves peptides derived from nerve growth factor receptor protein. Such peptides are characterized by competing for NGF binding to NGF receptor at high concentrations while accentuating NGF binding at low concentrations. Preferred peptides include Cys-Glu-Glu-Cys-Pro-Glu-OH, Asn-Thr-Val-Cys-Glu-Glu-Cys-Pro-Glu-OH, Gln-Asp-Lys-Gln-Asn-Thr-Val-Cys-Glu-Glu-Cys-Pro-Glu-OH and Cys-Gln-Asp-Lys-Gln-Asn-Thr-Val-Cys-Glu-Cys-Pro-Glu-OH.

3 Claims, 9 Drawing Sheets

OTHER PUBLICATIONS

Grob et al., "Affinity Labeling and Partial Purification of Nerve Growth Factor Receptors from Rat Pheochromocytoma and Human Melanoma Cells," *Proceedings of the National Academy of Science U.S.A.*, 80:6819–6823, 1983, published in U.S.A.

Hosang & Shooter, "The Internalization of Nerve Growth Factor by High–Affinity Receptors on Pheochromocytoma PC12 Cells," *The EMBO Journal, 6(5):1197–1202, 1987 published in Europe.*

Ullrich et al., "Sequence Homology of Human and Mouse β–NGF Subunit Genes," *Cold Spring Harbor Symposia on Quantitative Biology*, 48:435–442, 1983, published in U.S.A.

Kaplan et al., "The *trk* Proto–Oncogene Product: A Signal Transducing Receptor for Nerve Growth Factor," *Science*, 252:554–558, 1991 published in U.S.A.

Landreth & Shooter, "Nerve Growth Factor Receptors on PC12 Cells: Ligand–Induced Conversion from Low– to High–Affinity States," *Proceedings of the National Academy of Science U.S.A.*, 77(8):4751–4755, 1980, published in U.S.A.

DiStefano & Johnson, "Identification of a Truncated Form of the Nerve Growth Factor Receptor," *Proceedings of the National Academy of Science U.S.A.*, 85:270–274, 1988, published in U.S.A.

Massague et al., "Affinity Labeling of a Nerve Growth Factor Receptor Component on Rat Pheochromocytoma (PC12) Cells," *Biochimica et Biophysica Acta*, 693:205–212, 1982, published in The Netherlands.

Marchetti et al., "Nerve Growth Factor Receptors in Human Neuroblastoma Cells," *J. of Neurochemistry*, 49(2):475–486, 1987, published in New York.

Nebreda et al., "Induction by NGF of Meiotic Maturation of *Xenopus* Oocytes Expressing the *trk* Proto–Oncogene Product," *Science*, 252:558–561, 1991, published in USA.

Yan et al., "Chimeric NGF–EGF Receptors Define Domains Responsible for Neuronal Differentiation," *Science*, 252:561–563, 1991, published in USA.

Taniuchi et al., "Expression of Nerve Growth Factor Receptors by Schwann Cells of Axotomized Peripheral Nerves: Ultrastructural Location, Suppression by Axonal Contact, and Bindging Properties," *J. of Neuroscience*, 8(2):664–681, 1988, published in USA.

Mufson et al., "Loss of Nerve Growth Factor Receptor–Containing Neurons in Alzheimer's Disease: A Quantitative Analysis Across Subregions of the Basal Forebrain," *Experimental Neurology*, 105:221–232, 1989, published in USA.

Riopelle et al., "Properties of Receptors for Nerve Growth Factor in the Mature Rat Nervous System," *Molecular Brain Research*, 3:45–53, 1987, published in Netherlands.

Stach et al., "Binding of Nerve Growth Factor to Its Receptor," *J. of Neuroscience Research,"* 17:1–10, 1987, published in USA.

Angelucci et al., "Nerve Growth Factor Binding in Aged Rat Central Nervous System: Effect of Acetyl–L–Carnitine," *J. of Neuroscience Research*, 20:491–496, 1988, published in USA.

Goedert et al., "Nerve Growth Factor mRNA in Peripheral and Central Rat Tissues and in the Human Central Nervous System: Lesions Effects in the Rat Brain and Levels in Alzheimer's Disease," *Molecular Brain Research*, 1:85–92, 1986, published in the Netherlands.

Shan et al., "Reverse–Phase High–Performance Liquid Chromatography of Nerve Growth Factor Receptor–Like Proteins Identified With Monoclonal Antibodies," *J. of Neuroscience Research*, 27:620–632, 1990, published in USA.

Taglialatela et al., "Effects of Acetyl–L–Carnitine Treatment on Rat Pheochromocytoma PC12 Cells," Abstract No. 55, in *Transactions of the American Society for Neurochemistry*, 21(1):114, 1990 published in USA.

Dialog Search Report.

Marano et al., "Purification and amino terminal sequencing of human melanoma nerve growth factor receptor," *J. of Neurochemistry*, 48:225–232, 1987.

Hempstead et al., "Expression of functional nerve growth factor receptors after gene transfer,"*Science* 243:373–375, 1989.

Rossino et al., "Nerve Growth Factor Induces Increased Expression of a Laminin–Binding Integrin in Rat Pheochromocytoma PC12 Cells," *Dialog 55: Biosis Number: 90052486.*

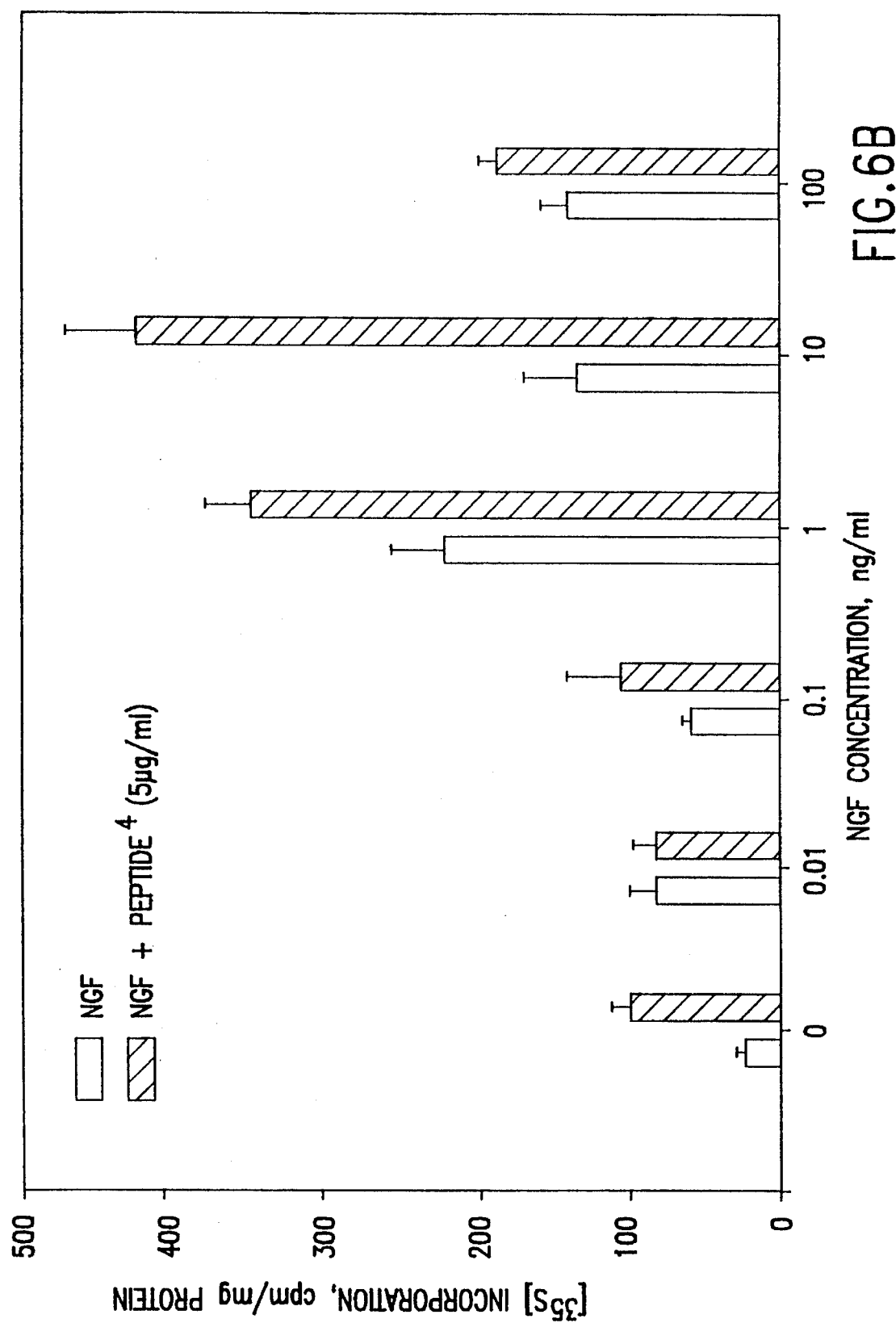

NEUROTROPHIC PEPTIDES

The United States government has certain rights in the present invention because research relating to its development was partially supported by funds supplied by the United States DHEW (NINDS of the NIH). This is a divisional of application Ser. No. 07/852,631, filed Mar. 17, 1992, now abandoned.

BACKGROUND OF THE INVENTION

The present invention relates to certain peptides of nerve growth factor receptor protein. These peptides may be used to accentuate stimulatory effects of nerve growth factor.

Neurons that successfully compete for target derived trophic factors, such as nerve growth factor, NGF, at critical stages in development, are spared cell death. Exogenous NGF, or its withdrawal by anti-NGF, has permanent effects on survival of peripheral and striatal neurons. The relationship between developmental neuronal cell death and its counterparts after injury and during aging in CNS is not known. NGF action has been best documented for sensory, sympathetic and magnocellular cholinergic neurons (MCN) of the basal forebrain (BF). There are two NGF binding activities with equilibrium dissociation constants ($K_d$) of $10^{-11}$M and $10^{-9}$M respectively. The former is a high affinity, low capacity binding site (NGFR-I) with a slow dissociation rate constant; the latter is a low affinity, high capacity site (NGFR-II) with a fast dissociation rate constant. Differences in NGFR are most likely due to the presence of an unidentified receptor-associated protein. Intraventricular injections of NGF in neonatal rats increases choline acetyl transferase (ChAT) activity in the basal forebrain, hippocampus, cortex, and the caudate nucleus. There are reported reductions in NGF and NGFR in cholinergic areas of the aged CNS. Since there is a reduction in trophic and principally NGF associated activity in those cholinergic regions that display aged associated pathology, it is not surprising that there have been found reductions in the NGF and NGF binding capacity in the aged rodent basal forebrain and hippocampus.

NGF is a neurotrophic protein whose structural features have been well-chronicled (Greene and Shooter, 1980; Levi-Montalcini, (1987). NGF has been purified from the submaxillary gland of mice and rats, murine saliva, several snake venoms, the guinea pig prostate, bovine seminal plasma, rodent seminal vesicle, and human term placenta (Perez-Polo, 1985). In some tissues, NGF has been isolated as a subunit containing protein. In all instances, only the β-NGF subunit, henceforth called NGF, has been found to have nerve growth promoting activity. To date, the role of the quaternary structure of NGF in the mouse submaxillary gland and the nature of the subunits' composition, if any, of NGF in neuronal tissues or not known (see Table 1).

TABLE 1

Studies on NGF

Biological variables studied

Neurite outgrowth
Cell hypertrophy
Cellular proliferation
Synaptogenesis
Cell survival
Cell death
Neurotransmitter expression
Neuro-immune-endocrine activation TABLE 1-continued Studies on NGF Biological phenomena of interest Development
Regeneration after spinal and head trauma
Chronic degenerative neurological dysfunction
Aging associated phenomena
Behavioral disorders The sequence of the α, β, and NGF genes is known, for β-NGF, the gene sequence is known for mouse, rat, bovine, human, and chick NGF, and all are highly conserved (Ebendal et al., 1986; Goedert, 1986; Isackson et al., 1987; Meier et al., 1986; Misko et al., 1987; Schwarz et al., 1989; .Scott et al., 1983; Ullrich et al., 1983a,b; Whittemore et al., 1988). The human gene for NGF is on the proximal short arm of chromosome 1 (Francke et al., 1983). Recombinant NGF has been characterized and shown to be biologically active (Bruce and Heinrich, 1989; Edwards et al., 1988). NGF mRNA levels have been determined for brain, superior cervical ganglia, and spinal cord, and correlated with NGF protein levels as a function of development, innervation, and response to injury (Auburger et al., 1987; Ayer-LeLievre et al., 1988; Goedert et al., 1986; Heumann et al., 1984, 1987; Korsching et al., 1985, 1986; Large et al., 1986; Lu et al., 1989; Rennert and Heinrich, 1986; Shelton and Reichardt, 1984). Although there is only one mature form of NGF expressed in the nervous system, there are two different precursor forms caused by differential RNA splicing (Edwards et al., 1986).

Levels of NGF mRNA and protein in the peripheral nerve system (PNS) and central nerve system (CNS) correlate with the density of sympathetic innervation (Korsching et al., 1985; Shelton and Reichardt, 1984). NGF mRNA and protein are widely distributed in CNS. The highest levels are in cortex and hippocampus, which are terminal regions for projections from basal forebrain cholinergic neurons. This is where NGF effects on ChAT induction and cell sparing, following lesions, have been best documented (Gnahn et al., 1983; Hefti et al., 1984; Mobley et al., 1986). It should be emphasized that, at early developmental stages, NGF and NGF receptor mRNA levels are highest in noncholinergic CNS structures, such as the cerebellum and outside the nervous system in the immune system (Buck et al., 1987, 1988; Ebendal et al., 1986; Ernfors et al., 1988; Large et al., 1986). It is not known what the role of NGF is during development, and these noncholinergic neurons do not remain NGF-responsive into adulthood (Dreyfus, 1989; Whittemore and Seiler, 1987).

NGF is one of a family of proteins called neurotrophins made up of NGF, brain derived neurotrophic factor (BDNF), NT3, and NT4. These share a 50–60% amino acid sequence homology, overlapping cellular targets in CNS and a common low affinity receptor species called $p75^{NGFR}$.

The first step of NGF action is the binding to specific membrane receptors (Banerjee et al., 1973; Frazier et al., 1973; Herrup and Shooter, 1973). In the PNS, two distinct NGF receptor (NGFR) sites have been found (Godfrey and Shooter, 1986). In the CNS, where NGF binding has not been as extensively characterized, preliminary reports would suggest that NGF binding activity has similar kinetic properties to its PNS counterparts (Angelucci et al., 1988z; Bernd et al., 1988; Cohen-Cory et al., 1989; Raivich and Kreutzberg, 1987; Taglialatela et al., 1990). It should be emphasized that, although the NGF receptor expressed by PC12 cells and some peripheral neurons has been partially characterized, less is known about the structural properties of NGFR expression in CNS and non-neural tissues. In part, this is as a result of the use of NGFR genetic probes based on the cDNA coding for only one of the NGF binding sites, the low affinity receptor (Radeke et al., 1987).

There are different ways to characterize NGF receptor activity. One method is to use receptor binding assays. Two NGF binding activities have been demonstrated for most neuronal tissues with equilibrium dissociation constants ($K_d$) of around $10^{-11}$ and $10^{-9}$M (Stach and Perez-Polo, 1987; Sutter et al., 1979). The former represents a high affinity, low capacity binding site (NGFR-I) that has a slow dissociation rate constant for ligand; the latter represents a low affinity, high capacity binding site (NGFR-II) that has a fast dissociation rate constant. It is generally believed that the NGFR-I is the physiologically relevant receptor present in neuronal populations (Green et al., 1986; Sonnenfeld and Ishii, 1985). Unfortunately, most demonstrations of high affinity NGF binding in the CNS have been indirect, and have relied on autoradiographic analysis of tissue sections exposed to $^{125}$I-NGF, and not on Scatchard analysis of specific, saturable binding of an NGF ligand (Cohen-Cory et al.,1989; Riopelle et al., 1987a,b; Yip and Johnson, 1987). The one exception would suggest that the proportion of low affinity sites to high affinity sites is greater outside the PNS making such an analysis difficult (Angelucci et al., 1988a; Taglialatela et al., 1990). It has been proposed that binding of NGF to the low affinity receptor converts it to its high affinity counterpart (Landreth and Shooter, 1980). There is also evidence that molecular species other than NGF can increase the proportion of high affinity receptors to NGF in isolated fractions of NGFR practically devoid of high affinity binding at the expense of the low affinity sites present there almost exclusively (Marchetti and Perez-Polo, 1987). The NGF-NGFR complex is internalized via high affinity binding mechanisms, a step thought to be necessary for NGF action, although there is no direct evidence for this (Bernd and Greene, 1984; Green et al., 1986; Hosang and Shooter, 1987).

A second approach that has been useful for the study of NGFR structure is sodium dodecyl sulfate polyacrylamide gel electrophoresis (SDS-PAGE) of $^{125}$I-NGF, which has been covalently crosslinked to NGFR. SDS-PAGE analysis has also been carried out on immunoprecipitated NGF-NGFR complexes, iodinated surface proteins of NGF responsive cells, and partially isolated NGFR enriched fractions relying on immunoaffinity chromatography, preparative isoelectric focusing, and reverse-phase high performance liquid chromatography, RP-HPLC (Beck et al., 1989; Buxser et al., 1985; Green and Greene, 1986; Grob et al., 1985; Hosang and Shooter, 1985; Kouchalakos and Bradshaw, 1986; Marano et al., 1987; Marchetti and Perez-Polo, 1987; Massague et al., 1982; Puma et al., 1983). Most descriptions of rodent NGFR are consistent with a 70–80 kD protein as the prevalent NGFR species, whereas, Puma et al., 1983 and Riopelle et al., 1987b, in human NGFR bearing cells, NGFR proteins of 92.5 kD have been reported. In both instances, there are higher molecular weight species of NGFR recognized. Kouchalakos and Bradshaw (1986) have analyzed the various reports for NGFR, and described a set of four different species of NGFR; class A (70–81 kD), Class B (87–105 kD), class C (120–145 kD), and class D (190–300 kD). The low affinity NGFR-II in PC12 cells, in human neuroblastoma LA-N-1 cells, and in human melanoma A875 cells was assigned to classes A and B. The larger molecular weight, NGFR in the class D category could be dimmer of the class B since their peptide maps are similar and there is some evidence for interconversion of the D to the B class under reducing conditions (Buxser et al., 1985; Grob et al., 1985; Marchetti and Perez-Polo, 1987). It is likely that B and C forms are part of one spectrum of biologically active NGFR, and A and D, respectively, represent truncated or aggregated forms (DiStefano and Johnson, 1988a,b). Ambiguities as to reported sizes may be the result of differences in the glycosylation or phosphorylation of NGFR, as well as of the many existing disulfide linkages present (Grob et al., 1983, 1985; Ross et al., 1984). Also, there is indirect evidence for a receptor associated protein with structural and functional effects on NGF binding (Hosang and Shooter, 1985; Marchetti and Perez-Polo, 1987). One difficulty here is that data from different tissues and species using different techniques are difficult to compare. It would appear that in most cases NGFR can be identified as two or more different molecular weight species.

The third approach to the characterization of NGFR relies on recombinant DNA technology. Both rat and human NGFR are the product of a single gene that does not appear to undergo differential splicing (Johnson et al., 1986; Large et al., 1989; Radeke et al., 1987). Based on the known NGFR DNA sequence, it has been determined that the human NGFR is synthesized as a precursor molecule with 427 amino acids (Johnson et al., 1986). The rat NGFR is highly homologous, and is a synthesized 425 amino acid precursor protein (Radeke et al., 1987). After removal of the N-terminal signal peptide, the protein core consists of 399 (human) or 396 (rat) amino acids, with an estimated molecular weight of 42 or 49 kD. The protein core is subsequently glycosylated to yield a 75–80 KD NGFR (Grob et al., 1985; Johnson et al., 1986). A second gene coding for the NGF receptor is the $p140^{protoirk}$ gene product of the trkA gene which is a membrane spanning 140 kDa tyrosine kinase that binds NGF. There is also a $p145^{trkb}$ gene product that binds BDNF and an NT3 binding species $p145^{trkC}$. The distribution and functions of these species in CNS is not definitively known but it would appear that whereas trkA is relevant to Alzheimer's disease, trkB is relevant to Parkinson's disease.

Receptors for NGF of $p75^{NGFR}$ variety are present on cells derived from all three germ layers, consistent with the hypothesis that NGF is not exclusively a neuronotrophic factor (Perez-Polo and Werrbach-Perez K., 1987; Thomson et al., 1988; Thorpe et al., 1987a,b,1989; Thorpe and Perez-Polo, 1987). For the CNS and PNS, NGFR and NGF mRNA expression appear to be coordinated and related to density of innervation (Buck et al., 1987; Korsching, 1986a,b; Whittemore and Seiler, 1987). There is NGF mRNA present in the hippocampus, cortex, thalamus/hypothalamus, brain stem, striatum, cerebellum, and spinal cord, in decreasing order. In some CNS regions, such as cerebellum, there is NGF and NGFR mRNA early in development not associated with cholinergic neurons (Whittemore and Seiler, 1987). The distribution of NGFR protein in the CNS is most evident in the hippocampus, frontal cortex, basal forebrain, and cerebellum (Angelucci et al., 1988a; Taniuchi et al., 1986a).

NGFRs are synthesized predominantly in the cell bodies of cholinergic neurons and subsequently transported via anterograde transport to the axon terminals (Buck et al., 1987). At the terminals, NGFR binds NGF, and the NGF-NGFR complex is internalized and retrogradely transported to neurons of the basal forebrain nuclei (Johnson et al., 1987; Seiler and Schwab, 1984). The continuous flux of NGF and NGFR, as well as, of the NGF-NGFR complex, may have regulatory significance on target tissues innervated, innervating neurons, or both (Hefti, 1986). However, NGF binding activity, NGFR protein, and NGFR mRNA in all regions of brain and lymphoid tissues, during some stages of development, have been reported for both the chick and the rat (Buck et al., 1988; Ernfors et al., 1988).

Three neuronal cell lines that have proven useful in the study of NGF are the PC12 rat pheochromocytoma line, the DK-N-SH-SY 5Y (SY5Y), and the LA-N-1 human neuroblastoma lines. The rat pheochromocytoma cell line PC12 is the most extensively studied NGF responsive cell line (Greene and Tischler, 1976). NGF has several major effects on PC12 cells that have been classified temporally and based on their RNA transcription dependence (Greene, 1984; Levi et al., 1988):

1. In common with other growth factors, NGF elicits rapid cell surface ruffling, stimulated ion fluxes across the cell membrane, and internalization of the NGF ligand (Connolly et al., 1979);

2. NGF induces short-term transcription-independent phosphorylation of several cytoplasmic proteins (Halegoua and Patrick, 1980; Romano et al., 1987); and transcription of some proto-oncogenes, such as c-myc, c-fos, and c-jun (Milbrandt, 1986, 1988; Wu et al., 1989);

3. NGF induces short-term synthesis of ornithine decarboxylase (Greene and McGuire, 1978);

4. NGF induces long-term transcription-dependent synthesis of those cytoskeletal proteins and cell adhesion molecules that are required for normal neurite growth; and 5. NGF can induce mitotic arrest under some conditions for PC12 cells.

This broad spectrum of responses is not unique to NGF, but rather, represents the response of the PC12 cell; other classes of NGF responsive cells may display a different spectrum of responses (Thorpe et al., 1989). Also, even for one cell line, such as the PC12 line, the different cell responses may not be coupled, and represent different segments of physiologically distinct outcomes. For some cell types like astrocytes and Schwann cells, ambient conditions can drastically affect the NGF response (Bothwell et al., 1980; Burstein and Greene, 1978, 1982; Green et al., 1986; Levi et al., 1988).

Human neuroblastoma cell lines are another model for studying the structure of NGFR and the effects of NGF (Perez-Polo and Werrbach-Perez, 1985, 1987). These cell lines are genetically stable, dependent on NGF for cell survival when grown in the absence of serum, and reversibly responsive to NGF. Similar to the findings in PC12 cells, treatment of neuroblastoma cells with NGF induces neurite outgrowth and hypertrophy (Perez-Polo et al., 1979; Sonnenfeld and Ishii, 1982), increases protein synthesis (Perez-Polo et al., 1982; Sonnenfeld and Ishii, 1982), and induces electrical excitability (Kuramoto et al., 1981). The study of NGF effects on neuroblastoma cells offers unique opportunities since the cells possess properties not present in PC12 cells.

First, only the high affinity NGFR-I type binding has been detected in neuroblastoma SY5Y cells (Sonnenfeld and Ishii, 1982, 1985). Second, SY5Y cells are reported to have NGFR mRNA of the same size as that reported for the low affinity NGF receptor and, when the SY5Y NGFR gene is transfected to mouse fibroblast-like L cells, the receptor expressed is also the NGFR-II type (Chao et al., 1986; Hempstead et al., 1989). This implies that, in SY5Y cells, there may exist a specific cellular environment that is responsible for the expression of the NGFR gene as an NGFR protein expressing high affinity binding.

Nerve growth factor (NGF) regulates neuronal cell death, neurite extension, and synapse formation during the development of sensory and sympathetic ganglia, and is also trophic to some neurons in the central nervous system (Levi-Montalcini, 1987; Thoenen and Barde, 1980; Whittemore and Seiler, 1987). The role played by NGF in the PNS has been well established and extensively reviewed (Greene and Shooter, 1980; Levi-Montalcini, 1987). During neuronal development, increased ambient levels of NGF in the region of the developing neurons provide guidance to outgrowing neuronal fibers in a process that may involve increased synthesis of NGF and NGFR by Schwann cells (Assouline and Pantazis, 1989; DiStefano and Johnson, 1988b). Once target tissues are innervated, Schwann cell synthesis, secretion of NGF and NGFR is curtailed, and target derived NGF is taken up at nerve terminals and retrogradely transported to the soma to maintain the differentiated state of the neuron (see FIG. 1 and Tables 5 and 6)(Hamburger And Oppenheim, 1982; Levi-Montalcini, 1987).

Although less is known about the role of NGF in the development of the CNS, there is evidence that it provides trophic support to basal forebrain cholinergic neurons (Gnahn et al., 1983; Hefti et al., 1984; Whittemore and Seiler, 1987; Williams et al., 1986). For example, NGF is synthesized in hippocampus and frontal cortex, and released in the proximity of nerve terminals of the basal forebrain where it is bound by NGFR, internalized, and retrogradely transported to mostly, but not only, the cholinergic neurons of the basal forebrain nuclei (Johnson et al., 1987). After fimbria-fornix transection, a lesion that interrupts the NGF-NGFR flux between the hippocampus and the basal forebrain, the cholinergic neurons of the diagonal band of Broca and septum undergo rapid cell death or severe cell shrinkage. Exogenous administration of NGF prevents this phenomenon in rats, when the fimbria-fornix has been severed or aspirated, thus demonstrating that the cell death exhibited by the cholinergic neurons of the basal forebrain under these conditions is likely caused by the lack of retrogradely transported NGF of hippocampal origin (Hefti, 1986; Will and Hefti, 1985; Williams et al, 1986). In aged humans and rats, there are deficits in NGF and NGFR (Angelucci et al., 1988b; Gomez-Pinilla et al., 1989; Hefti and Mash, 1989; Koh and Loy, 1988; Larkfors et al., 1987; Mufson et al., 1989a,b). The intraventricular infusion of NGF into aged rats rescues septal cholinergic neurons and improves behavioral performances in a spatial orientation task (Fischer et al., 1987).

It must be remembered that NGFR is also expressed in noncholinergic area of the brain and spinal cord, where it may play different roles in development, such as the regulation of cell migration (Schatteman et al., 1988) and neurite outgrowth (Collins and Dawson, 1983). Also, not all NGF-responsive tissues are in the nervous system. NGF has been shown to act as a mitogen on cultured chromaffin cells (Aloe and Levi-Montalcini, 1979; Lillien and Claude, 1985) and some classes of hemopoietic cells (Matsuda et al., 1988; Thorpe and Perez-Polo, 1987). Thus, different target cells respond to NGF in different fashions.

It has been established that, although neurons of the adult mammalian PNS are able to regenerate, the opposite is true for most of the CNS, in which abortive sprouting is more common (Ramon y Cajal, 1928). In those instances in the periphery, where it has been established that regeneration takes place, it has been demonstrated that ambient conditions under the control of Schwann and satellite cells are permissive for axonal sprouting, growth, and synaptogenesis. In the periphery, neurons that are isolated from target tissues, for example as a consequence of injury, exhibit a more rigorous dependence on the appropriate survival factors. Also, a procession of metabolic changes takes place in the Schwann and satellite cells, such as expression of NGF and NGFR mRNA, among others, that may account in part for the success of regeneration in the periphery, as compared to the CNS. The time sequelae involved in these injury induced changes in the nonneuronal cells of the periphery may be one of the important factors that differentiate the PNS from the CNS with respect to regeneration. Less is known about the molecular signals that act on glial and mast cells as part of the inflammation, gliosis, and scarring associated with neuronal injury. Thus, manipulations of ambient levels of neuronotrophic substances, and of other time-dependent events involved in the neuronal response to injury may answer the question of whether external manipulation of the organism can overcome the inability of the CNS to recover functionally from certain traumatic injuries.

There may be a correlation between cognitive deficits expressed in the aged and the levels of trophic activity in cholinergic areas of the CNS, as measured by the functional levels of critical growth factors, such as NGF and their receptors (Cortes et al., 1989; Eldridge et al., 1989 a,b; Flood and Coleman, 1988; Gage et al., 1988; Gomez-Pinilla et al., 1989; Hefti and Mash, 1989; Koh and Loy, 1988; Lahtinen, 1989; Larkfors et al., 1987, 1988; Mufson et al., 1989 a,b; Pezzoli et al., 1988). Since there is a reduction in trophic and principally NGF associated activity in those cholinergic regions that display age-associated pathology (Gomez-Pinilla et al., 1989; Hefti and Mash, 1989; Koh and Loy, 1988; Kudo et al., 1989; Larkfors et al., 1988; Mufson et al., 1989 a,b), it is not surprising that there is a reduction in the NGF and NGF binding capacity in the neurons of the aged rodent basal forebrain and hippocampus in the CNS, as well as in sympathetic neurons in the PNS (Angelucci et al., 1988a; Uchida and Tonionaga, 1987). Similar deficits in NGF and NGFR protein and mRNA have also been demonstrated in the CNS although, at the present time, it is not known if these deficits are a consequence of neuronal atrophy and cell loss there, or are a cause of such cell loss and atrophy (Flood and Coleman, 1988). It has been suggested that addition of exogenous NGF may reverse some cognitive deficits in the aged (Phelps et al., 1989).

It is not known if the mechanism by which NGF rescues basal forebrain cholinergic neurons following deafferentation lesions in the adult is the same as that by which NGF has sparing effects on aged rat cholinergic neurons of the CNS. It is difficult to speculate as to differences in the possible mechanisms of cell death, such as death resulting from neuronal injury as discussed here and cell death among NGF responsive neurons in the aged CNS. It is encouraging that acetyl-L-carnitine, a substance that ameliorates some age-associated cognitive deficits in aged rodents (Angelucci et al., 1986; Angelucci and Ramacci, 1986) and that appears to prevent age-associated decreases in NGF binding in hippocampus and basal forebrain (Angelucci et al., 1988), can also stimulate NGF binding activity in PC12 cells (Taglialatela et al., 1990 a,b). Although the precise mechanism by which acetyl-L-carnitine stimulates NGFR expression is not known, it is likely to be a general stimulation of trophic activity in the CNS acting by appropriate increased receptor expression.

SUMMARY OF THE INVENTION

The present invention involves peptides derived from the nerve growth factor receptor protein $p75^{NGFR}$. Such peptides are characterized by competing for NGF binding to NGF receptor at high concentrations while accentuating NGF binding at low concentrations. Preferred peptides include Cys-Glu-Glu-Cys-Pro-Glu-OH, SEQ ID NO: 1 Asn-Thr-Val-Cys-Glu-Glu-Cys-Pro-Glu-OH, SEQ ID NO: 2 Gln-Asp-Lys-Gln-Asn-Thr-Val-Cys-Glu-Glu-Cys-Pro-Glu-OH SEQ ID NO: 3 and Cys-Gln-Asp-Lys-Gln-Asn-Thr-Val-Cys-Glu-Glu-Cys-Pro-Glu-OH SEQ ID NO: 4.

The nerve growth factor receptor peptides of the present invention comprise an amino acid sequence preferably derived from the extracellular domain of nerve growth factor receptor protein, $p75^{NGFR}$ particularly between positions 110 and 123. These peptides may be utilized to accentuate neuronal stimulation effects of nerve growth factor. Such accentuation is accomplished, for example, by contacting neurons in the presence of endogenous nerve growth factor with peptide segments of nerve growth factor receptor protein. Because of the commonality of use of $p75^{NGFR}$ by NGF, BDNF and NT3, it may be that the aforementioned peptides also enhance BDNF and NT3 binding to their respective receptors.

Animal model experiments described herein illustrate that, in neurotoxic lesions of the type commonly utilized as models for Parkinson's Disease and Alzheimer's Disease, treatment of neuronal cells transplanted into regions of lesion are positively affected by pretreatment by NGF in the presence of a peptide of the present invention. It is noted that treatment of the cells to be transplanted with the peptides of the present invention results in subsequently greater concentrations of NGF receptor protein on cell surfaces. Thus, those skilled in the art will understand that, to alleviate the symptoms of Alzheimer's Disease of Parkinson's Disease, the administration of a pharmaceutically acceptable composition comprising a therapeutically effective amount of the nerve growth factor receptor protein fragment which, at a low concentration, enhances binding of growth factor to nerve growth factor receptor while inhibiting said binding at higher concentrations enhances healthy neuronal growth. Such healthy neuronal growth is useful for treating such patients and alleviating the disease syndrome. Parenteral administration of the peptides of the present invention and particularly intracysternal administration is effective.

BRIEF DESCRIPTION OF THE DRAWINGS

FIG. 6B shows that P4 has trophic effects on PC12 cell protein synthesis activity.

DESCRIPTION OF THE PREFERRED EMBODIMENTS

Figure 1:
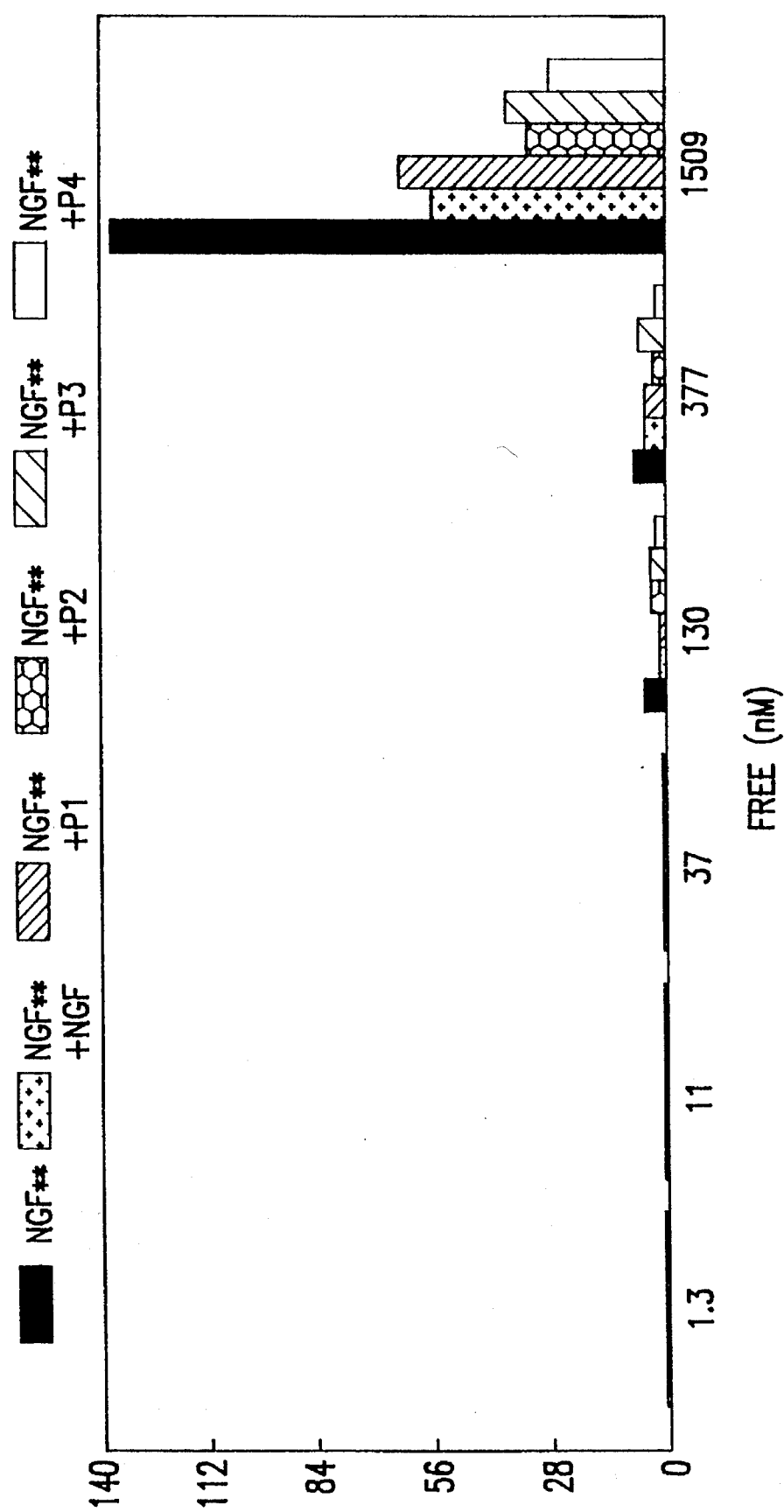
FIG. 1 shows that excesses of peptides (except for P1) are not as effective as NGF in displacing labelled NGF.

Because NGF molecules may not cross the blood brain barrier easily and also because treatment with NGF may lead to immunological complications, the present invention relates to ways of enhancing NGF activity. The present inventor found that certain segments of NGF receptor protein surprisingly stimulated NGF binding and activity at low concentrations while inhibiting said binding or activity at higher concentrations. Since synthetic peptides are much smaller in size than NGF and are therefore more amenable to passing the blood/brain barrier when desired and also less likely to elicit immunological responses.

The following examples are meant to set forth specific preferred embodiments and are not meant to limit the invention unless otherwise specified in the claims.

EXAMPLE 1

Peptides

The particular peptides utilized in these examples are shown in Table 2. These peptides were synthesized via a solid phase peptide synthesizer and their sequences derived from rat nerve growth factor receptor protein.

Peptide P1 is assigned the sequence identifier SEQ ID NO: 1, similarly, P2 is assigned SEQ ID NO: 2, P3 is assigned SEQ ID NO: 3, P4 is assigned SEQ ID NO: 4 and P5 is assigned the sequence identifier SEQ ID NO: 5.

EXAMPLE 2

Methods of the Present Invention

Cell Culture. Stock cultures of PC12 cells are maintained in a medium consisting of RPMI 1640 supplemented with (v/v) 5% fetal calf serum and 5% horse serum ("complete medium"). At alternate feedings, media containing 1% PSN antibiotic mixture is used, consisting of 5 mg penicillin +5 mg streptomycin +10 mg neomycin/ml. Cells are grown in a humidified atmosphere containing 5% $CO_2$. Cells are split once weekly in a 1:12 ratio by vigorous shaking and trituration. For experiments, PC12 cells are dislodged by shaking, centrifuged at 800×g, diluted in Puck's saline, counted in a hemocytometer, and plated on poly-D-lysine coated polystyrene tissue culture pates. For experiments to be performed in defined, serum-free medium, a modification of the N1 medium of Bottenstein et al. is used consisting of RPMI 1640 supplemented with insulin 5 ug/ml, transferrin 5 ug/ml, 20 nM progesterone, 100 μM putrescine, and 30 nM sodium selenite. Cells are plated in complete medium and allowed to attach overnight before washing twice with serum-free RPMI and addition of N1 medium. For experiments examining effects of NGF on cell survival following serum deprivation, cells are plated in complete medium and allowed to attach overnight. Cells are then washed once with RPMI containing sheep anti-mouse beta-NGF to remove any residual NGF from serum. After washing once in RPMI, cells receive varying doses of NGF in RPMI. Media is changed on the third day of serum deprivation. On the fourth day, viability is assessed by $^{35}$S-methionine incorporation into trichloroacetic acid precipitable proteins. The effects of NGF on the response of PC12 cells to peptides is also examined by reduction of the dye 3,(4,5-dimethylthiazol-2-yl)-2,5-diphenyl-tetrazolium (MTT). For experiments using MTT, cells ($1 \times 10^4$) are plated on poly-D-lysine coated 6 mm wells (96 well plates). Cells are allowed to attach overnight before addition of NGF and/or peptide. After 24 hr, media is removed and replaced with RPMI 1640 medium without serum. Following a 24 hour recovery period, each well is incubated with MTT for 4 hours at 37° C. Formaxan crystals are then solubilized in isopropanol containing 0.04N HCl and plates read on an ELISA reader using test and reference wavelengths of 570 and 630 nm, respectively. All statistics are performed by computer-assisted methods using the Number Cruncher for Statistical Sciences (NCSS) package. Either Student's t-test or analysis of variance (ANOVA) followed by Fischer's least significant difference test are used.

TABLE

| | 110 | 111 | 112 | 113 | 114 | 115 | 116 | 117 | 118 | 119 | 120 | 121 | 122 | 123 |
|---|---|---|---|---|---|---|---|---|---|---|---|---|---|---|
| P1 | | | | | | | | | Cys | Glu | Glu | Cys | Pro | Glu—OH |
| P2 | | | | | | | Asn | Thr | Val | Cys | Glu | Glu | Cys | Pro—Glu—OH |
| P3 | | | | Gln | Asp | Lys | Gln | Asn | Thr | Val | Cys | Glu | Glu | Cys—Pro—Glu—OH |
| P4 | | | Cys | Gln | Asp | Lys | Gln | Asn | Thr | Val | Cys | Glu | Glu | Cys—Pro—Glu—OH |
| P5 | | Tyr | Cys | Gln | Asp | Lys | Gln | Asn | Thr | Val | Cys | Glu | Glu | Cys—Pro—Glu—OH |

Competitive binding assay. The following method of binding assay was carried out: precoat the 24-well plates were precoated with cytochrome C and the PC12 cells plated overnight as mentioned above. The $^{125}$I labeled NGF was added at 5 ng/ml in the presence of different doses of peptide from 4 ug/ml to 50 ug/ml. The result showed that at low levels some of the peptides increased the binding of NGF to its receptor on PC12 cells. One possible explanation for these results is that electrostatic forces might be involved in NGF when binding to its receptor. These peptides are very acidic and NGF is very basic. At high doses, they can block the NGF effect but at low concentrations they appear to bind to the NGF and make NGF more actively bind to its receptor.

Membrane discs were placed into wells of 96 well plate. Peptide (for example 265 ng/ul) was spotted on each disc. Series dilutions of peptide were used to assure the binding. The disc was dried at 37° C. (or 40° C.) for 1 hour. 1000 ul 4% BSA TBS was added to each well. An amount of labelled NGF was added to each well, followed by incubation in 4% BSA TBS. Each disc was washed 4 times with 200 ul TBS (5 minute interval). The discs were transferred to counting vial and counted.

Bioassay on PC12 cells. The method of bioassay is as follows. The 24-well plastic plates are precoated with cytochrome C at 1 mg/ml each well and incubated for 1 hour. PC12 cells are separated and coated on the plate about $(1-2) \times 10^5$ cells/ml in each well overnight. The cells are added in a preincubated mixture of different peptides and NGF in the amount of 100 ug/ml peptide to 2 ng/ml NGF. The results, compared with control in which there is only NGF or blank, indicate that high doses of peptides block NGF action and the PC12 cells do not show neurite extension. The four peptides showed the same effect. The peptides in the absence of NGF had no effect.

EXAMPLE 3

Competitive Binding Assays

Figure 2:
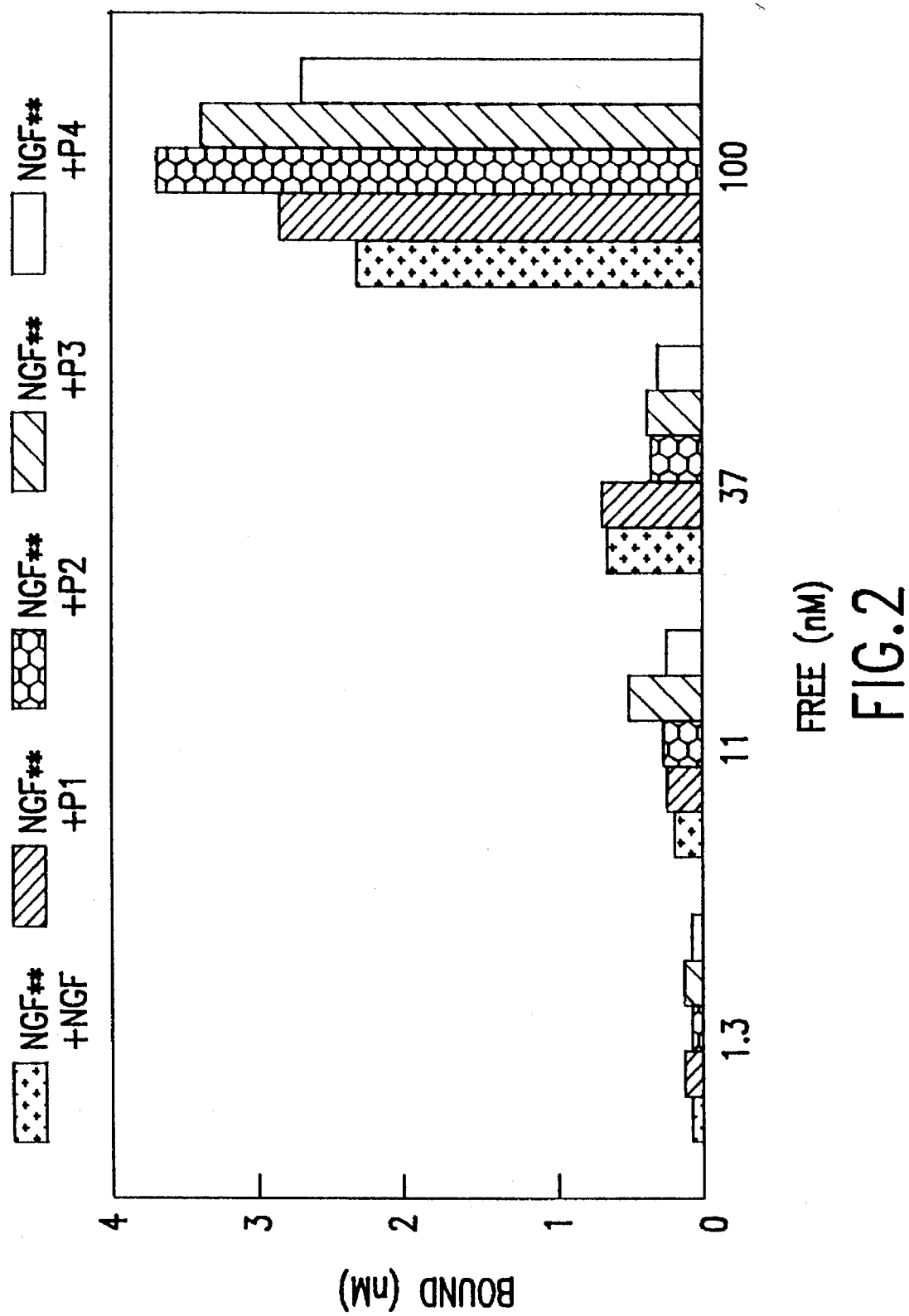
FIG. 2 illustrates how differing amounts of peptide displace labelled NGF from PC12 cells. As can be seen equimolar amounts of peptides at high concentrations can all equally displace NGF.

The 24 well plates were prepared as described in Example 2 (see section on the competitive binding assay.) FIG. 1 shows the binding of labeled NGF (NGF**) to the cells and the displacement of said labeled NGF by 10 micrograms of unlabeled NGF or 10 micrograms of the synthetic peptides P1–P4 at various concentrations of free labeled NGF. As might be expected, unlabeled NGF was more effective in displacing labeled NGF than most of the synthetic peptides. As shown in FIG. 2, at lower concentrations of free labeled NGF, all the synthetic peptides are still less effective than unlabeled NGF in labeled NGF displacement.

In another experiment 24-well plates were precoated with poly-D-Lys at 0.06 mg/ml for 15 minutes and PC12 cells plated overnight at $1 \times 10^5$ cells/well in RPMI 1640 with serum conditioned media. The $^{125}$I-NGF was added at, e.g., 5 ng/ml, in the presence of varying amounts of peptide from 0.01 ug/ml to 50 ug/ml in Hepes buffer with 1 mg/ml BSA. The cells were incubated at rt. for 1 hour then washed with PBS three times and lysed with 0.5N NaOH. The radioactivity was then measured. Protein concentrations of the aliquots were determined by Lowry assay. The results showed that at low levels of peptide, around 0.1 to 1 ug/ml, there was an increase in the binding of NGF to its receptor. For P1 there was no effect noted. For P2 and P3 the binding increased by 10% at 1 ug/ml. For P4 the binding increased by 50% within the 0.01–0.1 ug/ml range.

EXAMPLE 4

PC12 Cell Survival

Figure 3:
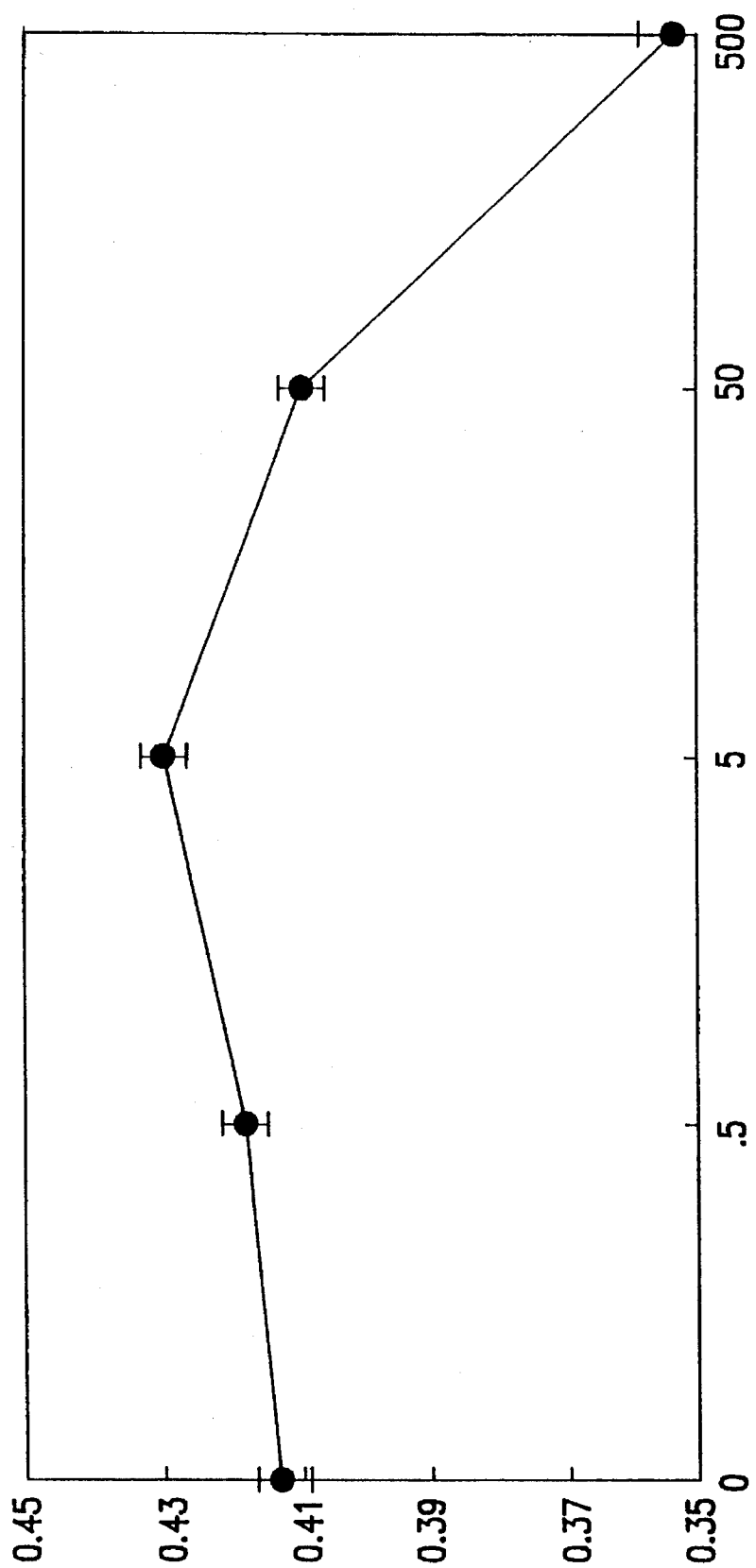
FIG. 3 shows how differing amounts of peptide 4 affect the survival of PC12 cells in the presence of 2 ng/ml of NGF.

The survival of PC12 cells was measured as a function of the amount of peptide P4. Should be noted that maximal cell survival was noted at the concentration of 5 µg peptide P4 (See FIG. 3). P3 was not as effective as P4. P1 and P2 did not demonstrate cell survival accentuation.

EXAMPLE 5

NGF Binding to P4

Figure 4:
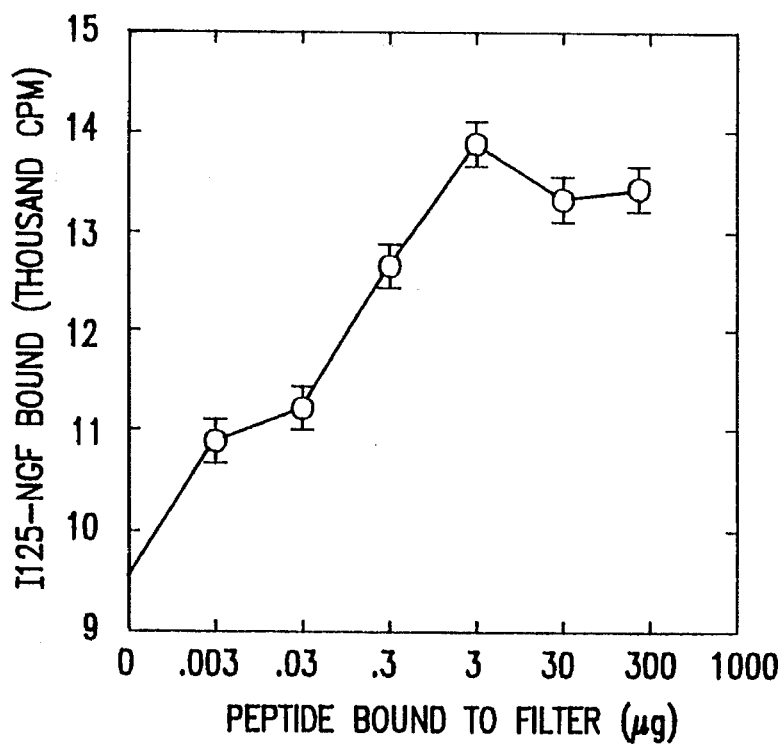
FIG. 4 illustrates how differing amounts of peptide bound differing amounts of labelled NGF.

Peptide P4 was attached to a solid matrix at various concentrations and the binding of labeled NGF measured to these various concentrations of bound P4. It is noted that an apparent maximal binding was achieved when about 3 µg of peptide P4 were bound. FIG. 4 illustrates how differing amounts of peptide bound differing amounts of labelled NGF. Here the peptide is fixed to a filter in varying amounts, then exposed to constant amounts of labelled NGF and washed extensively to displace unspecifically bound radioactivity. A saturation indicative of specific binding of NGF to peptide is seen which suggests an interaction between the two molecules. The specific augmentation of NGF effects may thus be understood when small amounts of peptide are added.

EXAMPLE 6

Effects of P3 and P4 on NGF Binding to PC12 Cells

Figure 5:
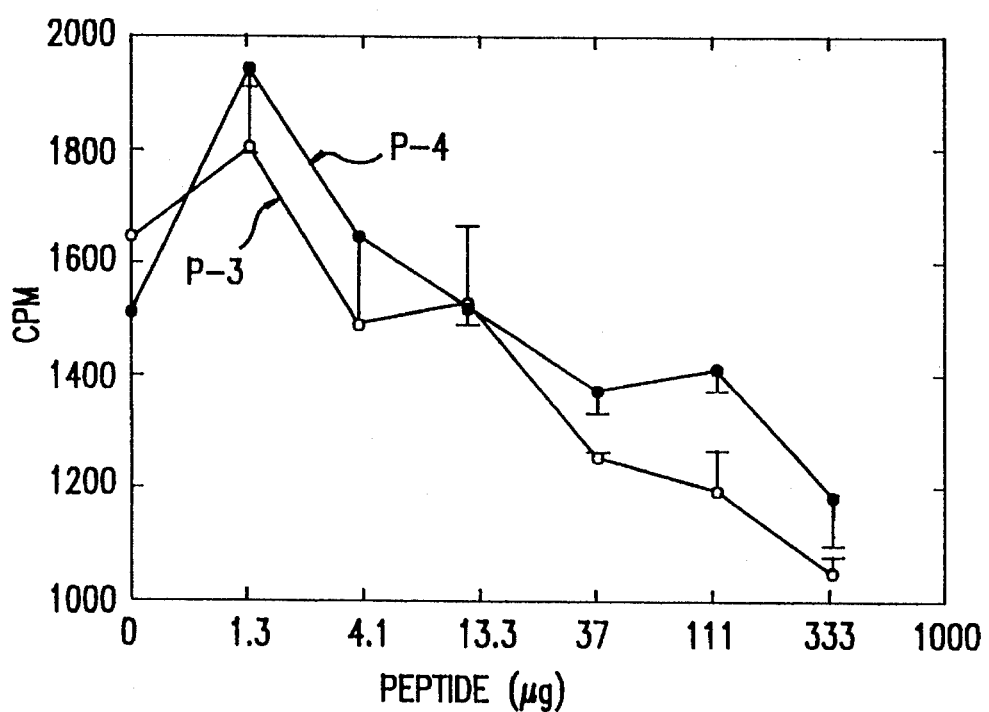
FIG. 5 demonstrates how differing amounts of peptide displace labelled NGF that is bound to PC12 cells.

At concentrations higher than about 1.5 µg, peptides P3 and P4 are effective in displacing bound labeled NGF from PC12 cells. At the lower concentrations measured (1.3 µg) the binding of labeled NGF was amplified. FIG. 5 demonstrates how differing amounts of peptide displace labelled NGF that is bound to PC12 cells. There is an increase in binding at the lower concentrations and then, due to competition, a decrease. Neither P1 nor P2 had any positive effect.

EXAMPLE 7

P5 Rescue of PC12 Cells from Serum Deprivation

Cells were plated out as mentioned above in RPMI 1640 without serum but in the presence of a fixed amount of NGF with varying amounts of peptide from 0.1 to 100 ug/ml (day one). On day three, the serum free medium was changed as on day one. On day four, the medium was replaced with 2 uCi/ml $^{35}$S-Met, Met free conditioned medium for 4 hours at 37° C. Cells were lysed with NaOH. The incorporation of $^{35}$S-Met into protein was determined by TCA precipitation and protein assay. The result showed that P4 peptide could increase protein synthesized by 20% at 0.1 ug/ml and could increase cell survival by 100% as compared to controls. For P1, P2 and P3 there was no significant change noted.

Figure 6:
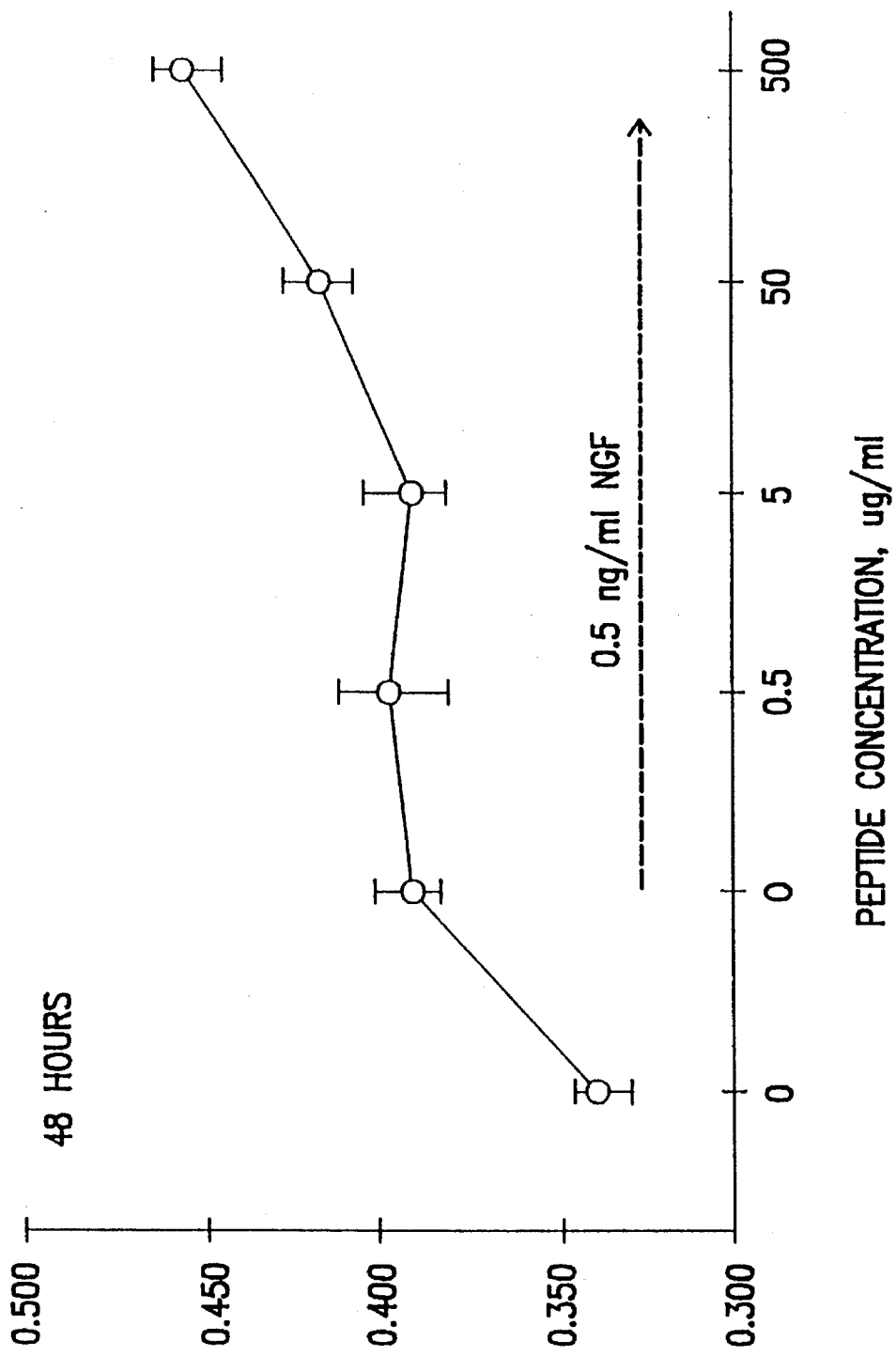
FIG. 6 shows the effect of P5 on PC12 survival in the presence of 0.5 ng/ml NGF.

FIG. 6 shows the effects of P5 peptide concentration upon PC12 cell survival during subjection to serum deprivation in the presence of 0.5 ng/ml NGF. An enhancement of cell survival is noted.

Figure 6A:
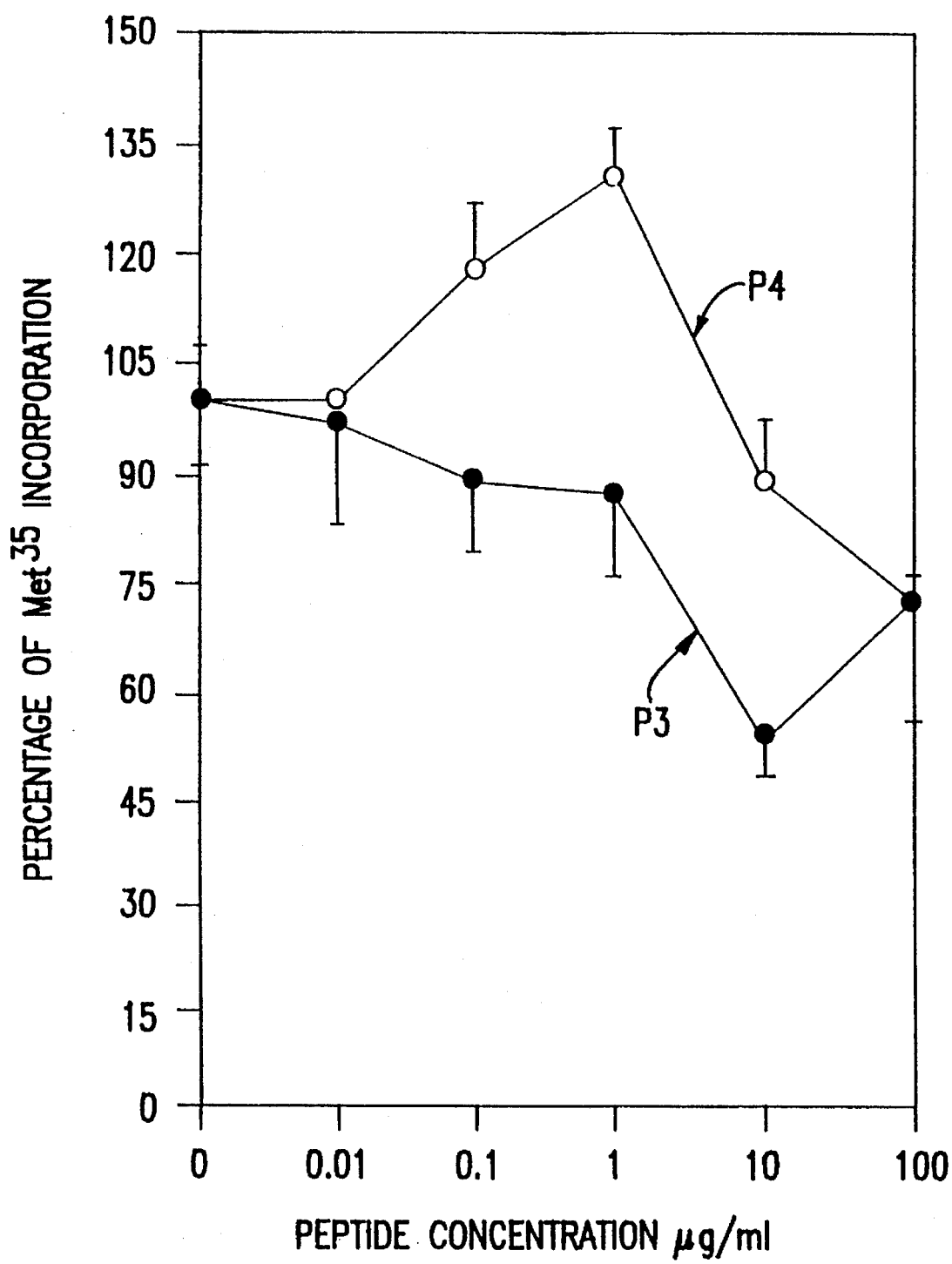
FIG. 6A shows that P4 is more effective than P3 for protein synthesis stimulation in the presence of 2 ng/ml of NGF.

FIG. 6A illustrates the effects of various levels of P3 and P4 in the presence of 2 ng/ml NGF on protein synthesis in PC12 cells in a serum-free medium. The stimulatory effects of P4 at from 0.1 to over 1 µg/ml are notable.

FIG. 6B demonstrates the trophic effects of P4 on PC12 cell protein synthesis activity at various NGF concentrations. Protein synthesis was measured by the extent of $^{35}$S-methionine incorporation into acid-precipitable material at NGF concentrations of 0.1 to 10 ng/ml (in the range of physiological NGF concentrations).

EXAMPLE 8

Immunostaining for Antibody Binding to Peptides

For the Dot-Blot Immunostaining Assay materials were prepared as follows:
1) 0.45 um nitrocellulose membrane discs (5 mm×5 mm/spot) 4 pieces
2) tissue culture plate 30 mm–60 mm
3) 1x BSA diluent/Blocking solution (10mg/ml) 50 ml
4) 1x washing solution with Tween-80 50 ml
5) conjugate antibody solution 0.1–2 ug (anti-rabbit IgG phosphatase, goat) in 1 ml 1x BSA Blocking solution
6) enzyme substrate (prepare immediately)
7) primary antibody solution: dilute primary antibody (1:50) in 1x BSA Blocking solution
8) distilled water The procedure for indirect antibody ELISA is briefly described as follows
1) Dot Blots
   a. wet membrane with water
   b. vacuum dry several hours or air dry 5–10 min
   c. apply 1 ul antigen (1–2 ug/ul)
   d. air dry 5 min
   e. immerse membrane into 1x BSA blocking solution for 30 min. rt. shaking
   f. remove membrane and blot excess solution on towel
2) React Primary Antibody
   a. transfer membrane into primary antibody solution incubate for 1 hr. rt. shaking.
   b. wash membrane 5 times, 5 min. and 2 ml each time
3) Add Second Antibody Conjugated with Enzyme
   a. transfer membrane into conjugate solution incubate 1 hr. rt.
   b. wash membrane 5 times, 5 min. and 2 ml each time
4) React Substrate with Bound Enzyme:
   a. transfer membrane into clean plate and cover with freshly prepared substrate solution, incubate at rt. until desired color intensity is developed in about 10 min.
   b. rinse with distilled water
   c. air dry at rt.

Figure 7:
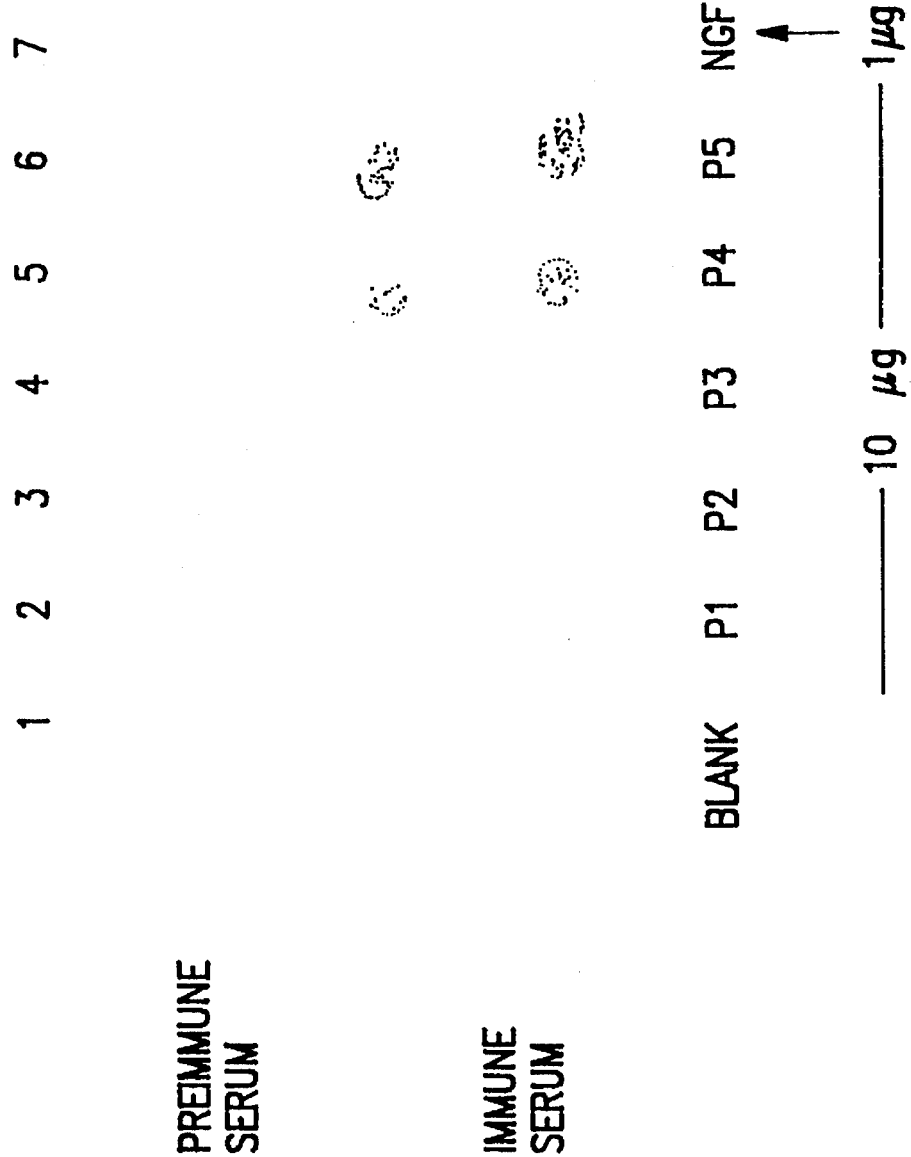
FIG. 7 shows the specificity of the antisera to peptide 4.

FIG. 7 shows the specificity of antisera to P4 for binding to peptides of the present invention. Note the antibody specificity for P4 and P5.

EXAMPLE 9

In vivo Enhancement of Neural Cells in Neurotoxic Lesions

Figure 8A:
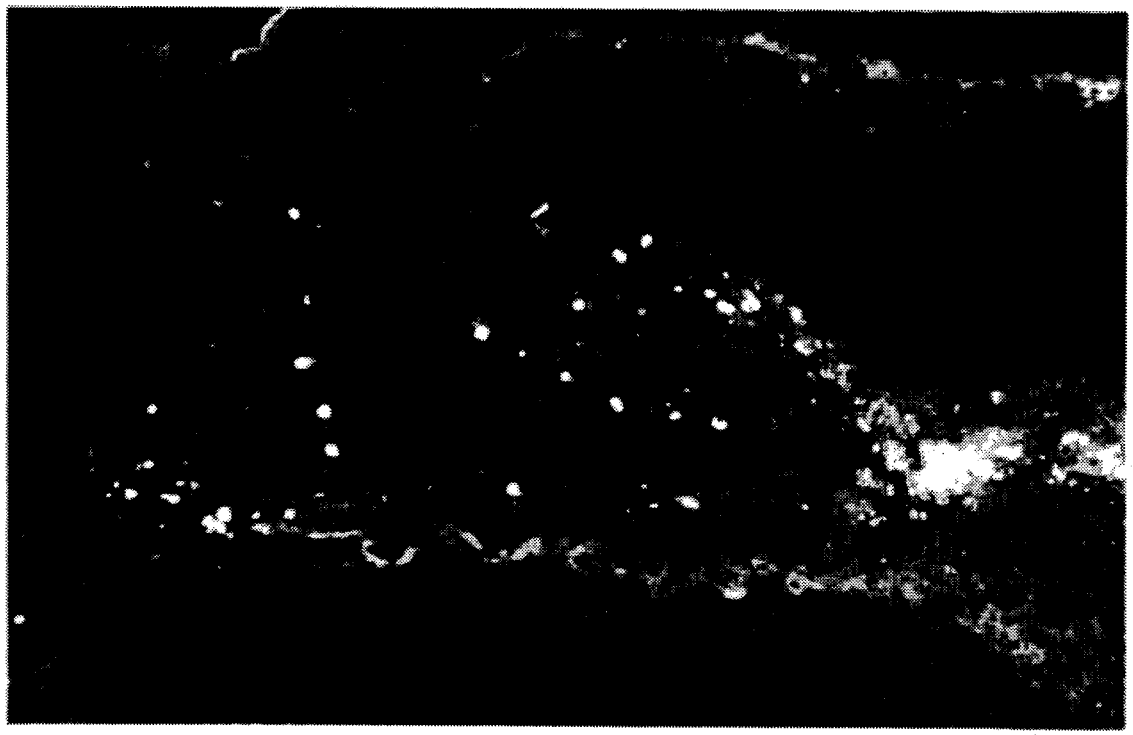
FIG. 8A shows PC12 cells treated with nerve growth factor in vitro for two weeks, followed by transplantation into rat cortex at the site of the stab wound.
Figure 8B:
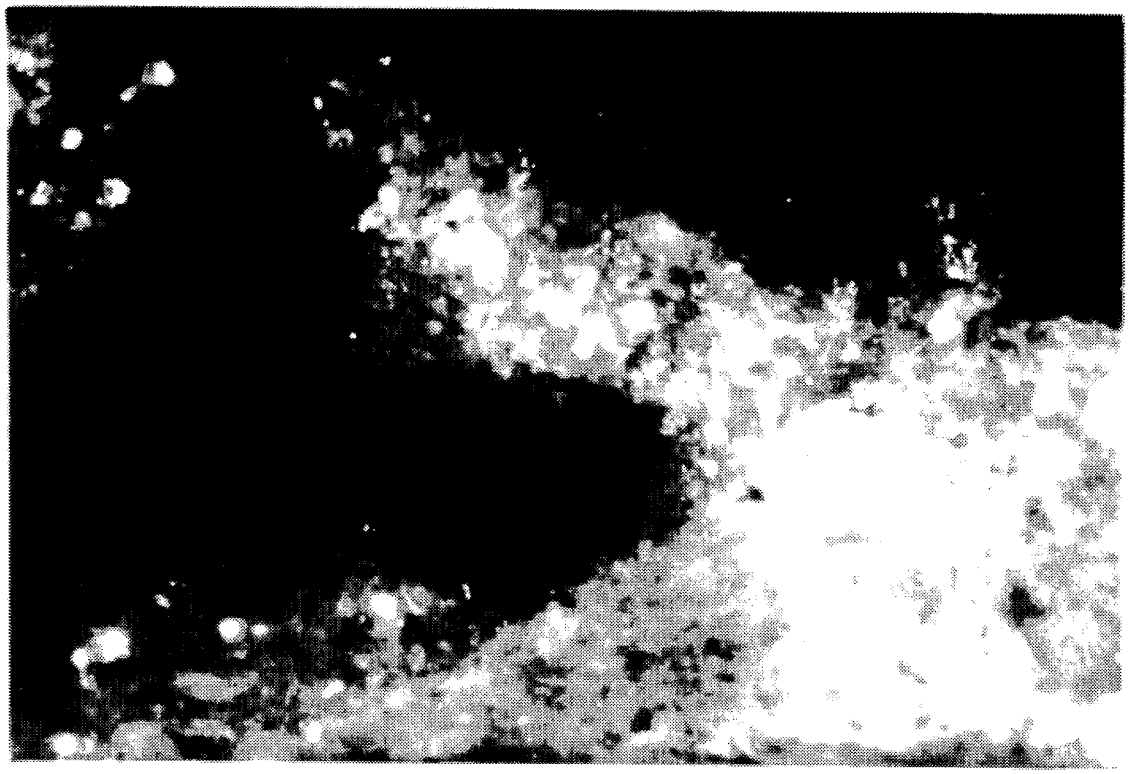
FIG. 8B shows PC12 cells treated with peptide P4 in vitro for two weeks and then transplanted into rat cortex at the site of the stab wound. Two weeks after the transplant, the brain was immunohistochemically processed with monoclonal antibody to NGF receptor (Ig192). It is noted that in FIG. 8B the PC12 cells exhibited a denser accumulation of NGF receptor sites. This increase is interpreted by experts to reflect enhanced survival of transplanted cells and a better interaction with host tissue. This increase would suggest that tissue to be transplanted into diseased brain should be pretreated with P4. This increase would suggest that P4 enhanced the ability of the host brain to survive the stab wound.

PC12 cells were treated with nerve growth factor (NGF) or peptide P4 in vitro for two weeks. The cells were then transplanted into a rat cortex at the site of the stab wound or 6-hydroxy dopamine-induced lesion. Two weeks after the transplant of the P12 cells, the animal brain was processed for immunohistochemistry by staining with monoclonal antibody to NGF receptor (Ig192). As seen by comparing FIG. 8A with FIG. 8B, cells which were also exposed to peptide P4 exhibited significantly greater NGF receptor. The stab-wound lesions carried out by inserting a 24 gauge needle into a stereotactically fixed animal so as to lesion motor cortex. Cells were then deposited with the same needle into the wound cavity.

Similar experiments were carried out with 6-hydroxydopamine-induced lesions, and with similar results. The 6-hydroxydopamine lesions were carried out by injecting 60 HDA stereotactically into striatum with a needle two weeks prior to transplantation and/or treatment of animals.

These experiments illustrate that neurocellular proliferation and/or biological integrity may be enhanced in vivo by treatment with peptides of the present invention.

The following literature citations are incorporated in pertinent part by reference herein for the reasons cited in the above text.

REFERENCES

Angelucci L., Ramacci M. T., Taglialatela G., Hulsebosch C., Morgan B., Werrbach-Perez K., and Perez-Polo J. R. (1988a) Nerve growth factor binding in aged rat central nervous system: Effect of acetyl-L-carnitine. *J. Neurosci. Res.* 20, 491–496.

Assouline J. G. and Pantazis N. J. (1989) Detection of a nerve growth factor receptor on fetal human Schwann cells in culture: Absence of the receptor on fetal human astrocytes. *Dev. Brain Res.* 45, 1–14.

Auburger G., Heumann R., Korsching S., and Thoenen H. (1987) Developmental changes of Nerve Growth Factor and its mRNA in rat hippocampus: Comparison with choline acetyl transferase. *Dev. Biol.* 120, 322–328.

Ayer-LeLievre C., Olson L., Ebendal T., Seiger A., and Persson H. (1988) Expression of the B-nerve growth factor gene in hippocampal neurons. *Science* 240, 1339–1341.

Banerjee S. P., Snyder S. H., Cuatrecasas P., and Greene L. A., (1973) Binding of nerve growth factor receptor in sympathetic ganglia. *Proc. Natl. Acad. Sci. USA* 70, 2519–2523.

Bernd P., Martinez H. J., Dreyfus C. F., and Black I. B. (1988) Localization of high-affinity and low-affinity nerve growth factor receptors in cultured rat basal forebrain. *Neurosci.* 26, 121–129.

Bothwell M. A., Schechter A. L., and Vaughn K. M. (1980) Clonal variants of PC12 pheochromocytoma cells with altered response to nerve growth factor. *Cell* 21, 857–866.

Bruce G. and Heinrich G. (1989) Production and characterization of biologically active recombinant human verve growth factor. *Neurobiol. Aging* 10, 89–94.

Buck C. R., Martinez H. J., Black I. B., and Chao M. V. (1987) Developmentally regulated expression of the nerve growth factor receptor gene in the periphery and brain. *Proc. Natl. Acad. Sci. USA* 84, 3060–3063.

Buck C. R., Martinez H. J., Chao M. V., and Black I. B. (1988) Differential expression of the nerve growth factor receptor gene in multiple brain areas. *Dev. Brain Res.* 44, 259–268.

Burnstein D. E. and Greene L. A. (1978) Evidence for RNA synthesis-dependent and -independent pathways in stimulation of neurite outgrowth by nerve growth actor. *Proc. Natl. Acad. Sci. USA* 75, 6059–6063.

Burnstein D. E. and Greene L. A. (1982) Nerve growth factor has both mitogenic and antimitogenic activity. *Dev. Biol.* 94, 477–482.

Buxser S., Puma P., and Johnson G. L. (1985) Properties of the nerve growth factor receptor. *J. Biol. Chem.* 260, 1917–1926.

Chao M. V., Bothwell M. A., Ross A. H., Korprowski H., Lanahan A. A., Buck C. R., and Sehgal A., (1986) Gene transfer and molecular cloning of the human NGF receptor. *Science* 232, 518–521.

Cohen-Cory S., Dreyfus C. F., and Black I. B. (1989) Expression of high- and low-affinity nerve growth factor receptors by purkinje cells in the developing rat cerebellum. *Exper. Neurol.* 105, 104–109.

Cortes R., Probst A., and Palacios J. M. (1989) Decreased densities of dopamine D1 receptors in the putamen and hippocampus in senile dementia of the Alzheimer type. *Brain Res.* 475, 164–167.

Dreyfus C. F. (1989) Effects of nerve growth factor on cholinergic Brain neurons. *TIPS* 10, 145–149.

DiStefano P. S. and Johnson Jr., E. M. (1988a) Identification of a truncated form of the nerve growth factor receptor. *Proc. Natl. Acad. Sci. USA* 85, 270–274.

DiStefano P. S. and Johnson Jr. , E. M. (1988b) Nerve growth factor and receptors on cultured rat Schwann cells. *J. Neurosci.* 8, 231–241.

Ebendal T., Larhammar D., and Persson H. (1986) Structure and expression of the chicken β-nerve growth factor gene. *EMBO J.* 5, 1483–1487.

Edwards R. H., Selby M. J., Mobley W. C., Weinrich S. L., Hruby D. E., and Rutter W. J. (1988) Processing and secretion of verve growth factor: Expression in mammalian cells with a vaccinia virus vector. *Mol. Cell. Biol.* 8, 2456–2464.

Eldridge J. C., Brodish A., Jute T. E., and Landfield P. W. (1989a) Apparent age-related resistance of Type II hippocampal corticosteroid receptors to down regulation during chronic escape training. *J. Neurosci* 9, 3237–3242.

Eldridge J. C., Fleenor D. G., Kerr D. S., and Landfield P. W. (1989b) Impaired upregulation of Type II corticosteroid receptors in hippocampus. *Brain Res.* 478, 248–256.

Ernfors P, Hallbook F., Ebendal T. , Shooter E. M., Radeke M. J., Misko T. P., and Person H. (1988) Developmental and regional expression of β-nerve growth factor receptor mRNA in the chick and rat. *Neuron* 1, 1988–1996.

Fischer W., Wictorin K., Bjorklund A., Williams L. R., Varon S., and Gage F. H. (1987) Amelioration of cholinergic neuron atrophy and spatial memory impairment in aged rats by nerve growth factor. *Nature* 329, 65–67.

Flood D. G. and Coleman P. D. (1988) Neuron numbers and sizes in aging brain: Comparisons of human, monkey and rodent data. *Neurobiol. Aging* 9, 453–463.

Francke U., De Martinville B., Coussens L., and Ullrich A. (1983) The human gene from the B subunit of nerve growth factor is located on the proximal short arm of chromosome 1. *Science* 222, 1248–1251.

Frazier W. A., Body L. F., and Bradshaw R. A. (1973) Interaction of nerve growth factor with surface membranes: Biological competence of insolubilized nerve growth factor. *Proc. Natl. Acad. Sci. USA* 70, 2931–2935.

Gnahn H., Hefti F., Heumann R., Schwab M. E., and Thoenen H. (1983) NGF-mediated increase of choline acetyltransferase (ChAT) in the neonatal rat forebrain: evidence for a physiological role of NGF in the brain. *Dev. Brain Res.* 9, 45–52.

Godfrey E. W. and Shooter E. M. (1986) Nerve growth factor receptors on chick embryo sympathetic ganglion cells: Binding characteristics and development. *J. Neurosci.* 6, 2543–2550.

Goedert M. (1986) Molecular cloning of the chicken nerve growth factor gene: mRNA distribution in developing and adult tissues. *Biochem. Biophys. Res. Commun.* 141, 116–1122.

Goedert M., Fine A., Hunt S., and Ullrich A. 1986) Nerve Growth Factor mRNA in peripheral nervous system and central nervous system and in human central nervous system: Lesion effects in rat brain and Alzheimer's disease. *Mol. Brain Res.* 1, 85–92.

Gomez-Pinilla F., Cotman C. W., and Nieto-Sampedro M. (1989) NGF receptor immuno-reactivity in aged rat brain. *Brain Res.* 1, 85–92.

Green S. H. and Greene L. A. (1986) a single M=103,000 $^{125}$I-β -nerve growth factor-affinity-labeled species represents both the low and high affinity forms of the nerve growth factor receptor. *J. biol. Chem.* 261, 15316–15326.

Greene L. A. and Shooter E. M. (1980) The nerve growth factor: Biochemistry, synthesis, and mechanism of action. *Ann. Rev. Neurosci.* 3, 353–402.

Grob P. M., Ross A. H., Koprowski H., and Bothwell M. (1985) Characterization of the human melanoma nerve growth factor receptor. *J. Biol. Chem.* 260, 8044–8049.

Halegoua S. and Patrick J. (1980) Nerve growth factor mediates phosphorylation of specific proteins *Cell* 22, 571–581.

Hamburger V. and Oppenheim R. W. (1982) *Cell Death. Neurosc. Comm.*1, 39–55.

Hefti F. and Mash D. C. (1989) Localization of nerve growth factor receptors in the normal human brain and in Alzheimer's disease. *Neurobiol. Aging.* 10, 75–87.

Hefti F., David A., and Hartikka J. (1984) Chronic intraventricular injections of nerve growth factor elevate hippocampal choline acetyltransferase activity in adult rats with partial septohippocampal lesions. *Brain Res.* 239, 305–311.

Hempstead B. L., Schleifer L. S., and Chao M. V. (1989) Expression of functional nerve growth factor receptors after gene transfer. *Science* 243, 373–375.

Herrup K. and Shooter E. M. (1973) Properties of the β-nerve growth factor receptor of avian dorsal root ganglia. *Proc. Natl. Acad. Sci. USA* 70, 3884–3888.

Heumann R., Korsching S., Scott J., and Thoenen H., (1984) Relationship between levels of nerve growth factor (NGF) and its messenger RNA in sympathetic ganglia and peripheral target tissues. *EMBO J.* 3, 3183–3189.

Heumann R., Linholm D. Bandtlow C., Meyer M., Radeke M. J., Misko T. P., Shooter E., and Thoenen H. 91987) Differential regulation of mRNA encoding nerve growth factor and its receptor in rat sciatic nerve during development, regeneration, and regeneration: Role of macrophages. *Proc. Natl. Acad. Sci. USA* 84, 8735–8739.

Hosang M. and Shooter E. M. (1987) The internalization of Nerve Growth Factor by high affinity receptors on pheochromocytoma PC12 cells. *EMBO J.* 6, 1197–1202.

Huebner K,. Isobe M., Chao M., Bothwell M., Ross a.H., Finan J., Hoxie J. A., and Sehgal A. (1986) The nerve growth factor receptor gene is a t human chromosome region 17q12–17q22, distal to the chromosome 17 breakpoint in acute leukemias. *Proc. Natl. Acad. Sci. USA* 83, 1403–1407.

Isackson P. J., Dunbar J. C., and Bradshaw R. A. (1987) Role of glandular kallikreins as growth factor processing enzymes: Structural and evolutionary considerations. *J. Cell Biochem.* 33, 65–75.

Johnson D., Lanahan A., Buck C. R., Sehgal A., Morgan C., Mercer E., Bothwell M., and Chao M. (1986) Expression and structure of the human NGF receptor. *Cell* 47, 545–554.

Koh S. and Loy R. (1988) Age-related loss of Nerve Growth Factor sensitivity in rat basal forebrain neurons. *Brain Res.* 440, 396–401.

Korsching S., Auburger G., Heumann R., Scott J., and Thoenen H. (1985) Levels of nerve growth factor and its mRNA in the central nervous system of the rat correlate with cholinergic innervation. *EMBO J.* 4, 1389–1393).

Korschiing S., Heumann R., Thoenen H., and Hefti F. (1986) Cholinergic denervation of the rat hippocampus by fimbirial transection leads to a transient accumulation of nerve growth factor (NGF) without change in mRNA content. *Neurosci. Lett.* 66, 175–180.

Kouchalakos R. N. and Bradshaw R. A. (1986) Nerve growth factor receptor from rabbit sympathetic ganglia membranes. *J. Biol. Chem.* 261, 16054–16059.

Kudo Y., Shiosaka S., Matsuda M., and Tohyama M. (1989) An attempt to cause the selective loss of the cholinergic neurons in the basal forebrain of the rat a new animal model of Alzheimer's disease. *Neuroscience Lett.* 102, 125–130.

Kuramoto T., Werrbach-Perez K., Perez-Polo J. R., and Haber B. (1981) Membrane properties of a human neuroblastoma II: Effects of differentiation. *J. Neurosci Res.* 6, 441–449.

Lahtinen T. (1989) age-dependence of the nerve fibre growth-promoting effects of hippocampus and exogenous nerve growth factor on cultured rat septum and superior cervical ganglion. *Cell Diff. Dev.* 26, 201–209.

Landreth G. E. and Shooter E. M. (1980) Nerve growth factor receptors on PC12 cells: Ligand-induced conversion from low- to high-affinity states. *Proc. Natl. Acad. Sci. USA* 77, 4751–4755.

Large T. H., Bodary S. C., Clegg D. O., Weskamp G., Otten U., and Reichardt L. F. (1986) Nerve growth factor gene expression in the developing rat brain. *Science* 234, 352–355.

Large T. H., Weskamp G., Helder J. C., Radeke M. J., Misko T. P., Shooter E. M., and Reichardt, L. F. (1989) Structure and developmental expression of the nerve growth factor receptor in the chicken central nervous system. *Neuron* 2, 1123–1134.

Larkfors L., Ebendal T., Whittemore S. R., Persson H., Hoffer B., and Olson L. (1987) Decreased level of nerve growth factor (NGF) and its messengers RNA in the aged rat brain. *Mol. Brain Res.* 3, 55–60.

Levi-Montalcini R., Aloe L., and Alleva E. (1990) A role for verve growth factor in nervous, endocrine and immune systems. *Progress in Neuroendocrine-Immunology* 3, 1–10.

Lillien L. and Claude P. (1985) Nerve Growth Factor mitogen for chromaffin cells. *Nature* 317, 632–634.

Lu B., Buck C. R., Dreyfus C. F., and Black I. B. (1989) Expression of NGF and NGF receptor mRNAs in the developing brain: Evidence for local delivery and action of NGF. *Exper. Neurol.* 104, 191–199.

Marano N., Dietzschold B., Earley J. J. Jr., Schatteman G., Thompson S., Grob P., Ross A. H., and Bothwell M. (1987) Purification and amino terminal sequencing of human melanoma nerve growth factor receptor. *J. Neurochem.* 48,225–232.

Marchetti D., Stach R. W., Saneto R. P., deVellis J., and Perez-Polo J. R. (1987) Binding constants of soluble Nerve Growth Factor receptors in rat oligodendrocytes and astrocytes in culture. *Biochem. Biophys. Res. Comm.* 147, 422–427.

Massague J., Buxser S., Johnson G. L., and Czech M. P. (1982) affinity labeling of a nerve growth factor receptor component on rat pheochromocytoma (PC12) cells. *Biochem. Biophys. Acta* 693, 205–212.

Matsuda H., Coughlin M. D., Bienenstock J., and Denburg J. (1988) Nerve growth factor promotes human hemopoietic colony growth and differentiation. *Proc. Natl. Acad. Sci. USA* 85, 6508–6512.

Meier R., Becher-Andre M., Gotz R., Heumann R., Shaw A., and Thoenen H. (1986) Molecular cloning of bovine and chick nerve growth factor (NGF): Delineation of conserved and unconserved domains and their relationship to the biological activity and antigenicity of NGF. *EMBO J.* 5, 1489–1493.

Milbrandt J. (1986) Nerve growth factor rapidly induces c-fos mRNA in PC12 rat pheochromocytoma cells. *Proc. Natl. Acad. Sci. USA* 83, 4780–4793.

Milbrandt J. (1988) Nerve growth factor induces a gene homologous 64 to the glucocorticoid receptor gene. *Neuron* 1, 183–188.

Misko T. P., Radeke M. J., and Shooter E. M. (1987) Nerve growth factor in neuronal development and maintenance. *J. Exp. Biol* 132, 177–190.

Mobley W. C., Rutkowski J. L., Tennekoon G. I., Gemski J., Buchanan K., and Johnston M. V. (1986) Nerve growth factor increases choline acetyl-transferase activity in developing basal forebrain neurons. *Mol. Brain Res.* 1, 53–62.

Mufson E. J., Bothwell M., Hersh L. B., and Kordower J. H. (1989a) Nerve growth factor receptor immunoreactive profiles in the normal, aged human basal forebrain: Colocalization with cholinergic neurons. *J. of Comp. Neurol.* 285, 196–217.

Mufson E. J., Bothwell M., and Kordower J. H. (1989b) Loss of nerve growth factor receptor containing neurons in Alzheimer' Disease: A quantitative analysis across subregions of the basal forebrain. *Exp. Neurol.* 105, 221–232.

Perez-Polo J. R. (1985) Neuronotrophic factors, in *Cell Cultures in the Neurosc.*, Plenum, N.Y. 3: pp.95–123.

Perez-Polo J. R. (1987) *Neuronal Factors*. CRC, Boca Raton, pp 1–202.

Perez-Polo J. R. and Werrbach-Perez K. (1987) In vitro model of neuronal aging and development in the nervous system, in *Model Systems of Development and Aging of the Nervous System* 1, Vernadakis A., ed., Martinus Nijhoff, Boston. pp. 433–442.

Perez-Polo J. R. , Werrbach-Perez K, and Tiffany-Castiglioni E. (1979) A human clonal cell line model of differentiating neurons. *Dev. Biol.* 71, 341–355.

Perez-Polo J. R., Tiffany-Castiglioni E., Ziegler M. G., and Werrbach-Perez K. (1982b) Effect of nerve growth factor on catecholamine metabolism in a human neuroblastoma clone (SY5Y). *Dev. Neurosci.* 5, 481–483.

Perez-Polo J. R., Reynolds C. P., Tiffany-Castiglioni E., Ziegler M., Schulze I., and Werrbach-Perez K. (1982a) NGF effects on human neuroblastoma lines: A model system, in *Proteins in the Nervous System: Structure and Function*, Haber B., Perez-Polo J. R. and Coulter J., eds., Liss, NY, pp. 285–299.

Pezzoli G., Fahn S., Dwork A., Truong D. D., De Yebenes J. G., Jackson-Lewis V., Herbert J., and Lud Cadet J. (1988) Nonchromaffin tissue plus nerve growth factor reduces experimental parkinsonism in aged rats. *Brain Res.* 459, 398–403.

Phelps C. H., Gage F. M., Growdon J. H., Hefti F. Harbaugh R., Johnston M. V., Khacheturian Z. S. Mobley W. C., Price D. L., Reskind M. Simpkins j. Thal L. J., and Woodcock J. (1989) Potential use of nerve growth factor to treat Alzheimer's Disease. *Neurobiol. Aging* 10, 205–207.

Puma P. Buxser S. E., Watson L., Kelleher D. J., and Johnson G. L. (1983) Purification of the receptor for nerve growth factor from A875 melanoma cells by affinity chromatography. *J. Biol. Chem.* 258, 3370–3375.

Radeke M. J., Misko T. P., Hasu C., Herzenberg L. A., and Shooter E. M. (1987) Gene transfer and molecular cloning of rat Nerve Growth Factor receptor. *Nature* 325, 593–597.

Rennert P. D. and Heinrich G. (1986) Nerve growth factor mRNA in Brain: Localization by in sutu hybridization. *Biochem. Biophys. Res. Commun.* 138, 813–818.

Rettig W. J., Thomson T. M., Spengler B. A., Biedler J. L., and Old L. J. (1986) Assignment of human nerve growth factor receptor gene to chromosome 17 and regulation of receptor expression in somatic cell hybrids. *Somat. cell. Molec. Genet.* 12, 441–447.

Riopelle R. J., Verge V. M. K., and Richardson P. M., (1987a) Properties of receptors for Nerve Growth Factor in the mature rat nervous system. *Mol. Brain Res.* 3, 45–53.

Riopelle R. J., Richardson P. M, and Verge V. M. K. (1987b) Distribution and characteristics of nerve growth factor binding on cholinergic neurons of rat and monkey forebrain. *Neurochem. Res.* 12, 923–928.

Romano C., Nichols R. A., and Greengard P. (1987) Synapse in I in PC12 cells. II. Evidence for regulation by NGF of phosphorylation at a novel site. *J. Neurosci* 7, 1300–1306.

Ross A. H., Grob P., Bothwell M., Elder D. E., Ernst C. S., Marano N., Ghrist B. F. D., and Slemp C. C. (1984) Characterization of nerve growth factor receptor in neural crest tumors using monoclonal antibodies. *Proc. Natl. Acad. Sci. USA* 81, 6681–6685.

Schattemen G. C., Gibbs L., Lanahan A. A., Claude P., and Bothwell M. (1988) Expression of NGF receptor in the developing and adult primate central nervous system. *J. Neurosci.* 8, 860–873.

Schwarz M. A., Fisher D., Bradshaw R. A., and Isackson P. J. (1989) Isolation and sequence of a cDNA clone of β-nerve growth factor from the guinea pig prostate gland. *J. Neurochem.* 52, 1203–1209.

Scott J., Selby M., Urdec M., Quirega M., Bell G. I., and Rutter W. J. (1983) Isolation and nucleotide sequence of a cDNA encoding the precursor of mouse nerve growth factor. *Nature* 302, 538–540.

Shelton D. L. and Reichardt L. F. (1984) Expression of the β-nerve growth factor gene correlates with the density of sympathetic innervation in effector organs. *Proc. Natl. Acad. Sci. USA* 81, 7951–7955.

Sonnenfeld K. H. and Ishii D. N. (1985) Fast and slow nerve growth factor binding sites in human neuroblastoma and rat pheochromocytoma cell lines: Relationship of sites to each other and to neurite formation. *J. Neurosci.* 5, 1717–1728.

Stach R. W. and Perez-Polo R. (1987) Binding of nerve growth factor to nerve growth factor receptor. *J. Neurosci. Res.* 17, 1–10.

Sutter a., Riopelle R. J., Harris-Warrick R. M., and Shooter E. M. (1979) Nerve growth factor receptors. *J. Biol. Chem.* 254, 5972–5982.

Taglialatela G., Angelucci L., Ramacci M. T., Teng, J., Werrbach-Perez K., and Perez-Polo J. R. (1990) Effects of acetyl-L-carnitine treatment on rat pheochromocytoma PC12 cells. *American Soc. Neurochem.* 21:1, 114.

Taniuchi M., Schweitzer J. B., and Johnson Jr., E. M. (1986a) Nerve growth factor receptor molecules in rat brain. *Proc. Natl. Acad. Sci. USA* 83, 1950–1954.

Thomson T. M. Rettig W. J., Chesa P. G., Greene S. H., Mena A. C., and Old L. J. (1988) Expression of human verve growth factor receptor on cells derived from all three germ layers. *Exp. Cell Res.* 174, 533–539.

Thorpe L. W. and Perez-Polo J. R. (1987) The influence of nerve growth factor on the in vitrol proliferative response of rat spleen lymphocytes. *J. Neurosci. Res.* 18, 134–139.

Thorpe L. W., Stach R. W., Hashim G. A., Marchetti D., and Perez-Polo, J.r. (1987a) Receptors for nerve growth factor on rat spleen mononuclear cells. *J. Neurosci. Res.* 17, 128–134.

Thorpe L. W., Werrbach-Perez K., and Perez-Polo J. R. (1987b) Effects of nerve growth factor on he expression of interleukin 2 receptors on cultured human lymphocytes. *Ann. NY Acad. Sci.* 496, 310–311.

Thorpe L. W., Stach R. W., Morgan B., and Perez-Polo J. R. (1989( The biology of nerve growth factor: Its interaction with cells of the immune system, in *Neural Control of Reproductive Function*, Lakoski J. M., Perez-Polo J. R., and Rassin D. K., eds., Liss, NY, pp. 351–369.

Uchida Y. and Tonionaga M. (1987) loss of Nerve growth factor receptors in sympathetic ganglia from aged mice. *Biochem. Biophys. Res. Comm.* 146, 797–801.

Ullrich A., Gray A., Berman C., Coussens L., and Dull T. J. (1983a) Sequence homology of human and mouse β-NGF subunit genes. *Cold Spring Harbor Symposia on Quantitative Biol.* 48, 435–442.

Ullrich A., Gray A., Berman C., and Dull T. J. (1983b) Human nerve growth factor gene sequence highly homologous to that of mouse. *Nature* 303, 821–825.

Wu B.-y., Fodor E. J. B., Edwards R. H., and Rutter W. J. (1989) Nerve growth factor induces the protooncogene c-jun in PC12 cells. *J. Biol. Chem.* 264, 9000–9003.

---

What is claimed is:

1. A peptide having the structure Gln-Asp-Lys-Gln-Asn-Thr-Val-Cys-Glu-Glu-Cys-Pro-Glu-OH.

2. A peptide having the structure Cys-Gln-Asp-Lys-Gln-Asn-Thr-Val-Cys-Glu-Glu-Cys-Pro-Glu-OH.

3. A peptide having the structure Tyr-Cys-Gln-Asp-Lys-Gln-Asn-Thr-Val-Cys-Glu-Glu-Cys-Pro-Glu-OH.

* * * * *

SEQUENCE LISTING ( 1 ) GENERAL INFORMATION:

( i i i ) NUMBER OF SEQUENCES: 5

( 2 ) INFORMATION FOR SEQ ID NO: 1:

( i ) SEQUENCE CHARACTERISTICS:
                    ( A ) LENGTH: 6 amino acid residues
                    ( B ) TYPE: amino acid
                    ( C ) STRANDEDNESS: Not Relevant
                    ( D ) TOPOLOGY: linear ( x i ) SEQUENCE DESCRIPTION: SEQ ID NO: 1:

Cys Glu Glu Cys Pro Glu
 1               5

( 2 ) INFORMATION FOR SEQ ID NO: 2:

( i ) SEQUENCE CHARACTERISTICS:
                    ( A ) LENGTH: 9 amino acid residues
                    ( B ) TYPE: amino acid
                    ( C ) STRANDEDNESS: Not Relevant
                    ( D ) TOPOLOGY: linear ( x i ) SEQUENCE DESCRIPTION: SEQ ID NO: 2:

Asn Thr Val Cys Glu Glu Cys Pro Glu
 1               5

( 2 ) INFORMATION FOR SEQ ID NO: 3:

( i ) SEQUENCE CHARACTERISTICS:
                    ( A ) LENGTH: 13 amino acid resdues
                    ( B ) TYPE: amino acid
                    ( C ) STRANDEDNESS: Not Relevant
                    ( D ) TOPOLOGY: linear ( x i ) SEQUENCE DESCRIPTION: SEQ ID NO: 3:

Gln Asp Lys Gln Asn Thr Val Cys Glu Glu Cys Pro Glu
 1               5                   10

( 2 ) INFORMATION FOR SEQ ID NO: 4:

( i ) SEQUENCE CHARACTERISTICS:
                    ( A ) LENGTH: 14 amino acid residues
                    ( B ) TYPE: amino acid
                    ( C ) STRANDEDNESS: Not Relevant
                    ( D ) TOPOLOGY: linear ( x i ) SEQUENCE DESCRIPTION: SEQ ID NO: 4:

Cys Gln Asp Lys Gln Asn Thr Val Cys Glu Glu Cys Pro Glu
 1               5                   10

( 2 ) INFORMATION FOR SEQ ID NO: 5:

( i ) SEQUENCE CHARACTERISTICS:
                    ( A ) LENGTH: 15 amino acid residues
                    ( B ) TYPE: amino acid
                    ( C ) STRANDEDNESS: Not Relevant
                    ( D ) TOPOLOGY: linear ( x i ) SEQUENCE DESCRIPTION: SEQ ID NO: 5:

Tyr Cys Gln Asp Lys Gln Asn Thr Val Cys Glu Glu Cys Pro Glu
 1               5                   10                  15